(12) United States Patent
Reddington

(10) Patent No.: US 7,868,157 B2
(45) Date of Patent: Jan. 11, 2011

(54) WATER SOLUBLE FLUORESCENT COMPOUNDS

(75) Inventor: Mark Reddington, San Francisco, CA (US)

(73) Assignee: Biosearch Technologies, Inc., Novato, CA (US)

( * ) Notice: Subject to any disclaimer, the term of this patent is extended or adjusted under 35 U.S.C. 154(b) by 0 days.

(21) Appl. No.: 11/482,288

(22) Filed: Jul. 7, 2006

(65) Prior Publication Data

US 2007/0021621 A1 Jan. 25, 2007

Related U.S. Application Data

(60) Provisional application No. 60/697,314, filed on Jul. 7, 2005, provisional application No. 60/712,301, filed on Aug. 30, 2005.

(51) Int. Cl.
- *C07H 21/04* (2006.01)
- *C07K 5/00* (2006.01)
- *C07D 209/02* (2006.01)
- *C12Q 1/68* (2006.01)

(52) U.S. Cl. ............... 536/24.3; 530/300; 530/802; 548/455; 435/6

(58) Field of Classification Search ............... None
See application file for complete search history.

(56) References Cited

U.S. PATENT DOCUMENTS

| | | | |
|---|---|---|---|
| 3,493,639 | A | 2/1970 | Tavs |
| 4,150,021 | A | 4/1979 | Swidler et al. |
| 5,268,486 | A | 12/1993 | Waggoner et al. |
| 5,486,616 | A | 1/1996 | Waggoner et al. |
| 5,877,310 | A | 3/1999 | Reddington et al. |
| 6,348,599 | B1 | 2/2002 | Cummins et al. |
| 6,706,879 | B2 * | 3/2004 | Anderson et al. ......... 546/88 |
| 2005/0272088 | A1 | 12/2005 | Cook et al. |
| 2006/0035262 | A1 | 2/2006 | Cook et al. |

OTHER PUBLICATIONS

Gale, et al., "The Amidomethylation and Bromination of Fischer's Base. The Preparation of Some New Polymethine Dyes," *Australian J. Chem*, 1977, 30:689-694.
Devlin, et al., "Homogeneous Detection of Nucleic Acids by Transient-State Polarized Fluorescence," *Clin. Chemistry*, 1993, 39(9):1939-1943.
Spatola, A.F., *Chemistry and Biochemistry of Amino Acids, Peptides and Proteins*, B. Weinstein, eds., Marcel Dekker, New York, vol. 7, p. 267-357 (1983).
Still, et al., "Rapid Chromatographic Technique for Preparative Separations with Moderate Resolution," *J. Org. Chem.*, 1978, 43(14):2923-2925.
Southwick, et al., "Cyanine Dye Labeling Reagents—Carboxymethylindocyanine Succinimidyl Esters," *Cytometry*, 1990, 11:418-430.
Borbas, K.E., et al., "Bioconjugatable Porphyrins bearing a Compact Swallowtail Motif for Water Solubility" *Bioconjugate Chemistry*, 17:638-653 (2006).
Gale, et al., "The Amidomethylation and Bromination of Fischer's Base. The Preparation of Some New Polymethine Dyes," *Aust. J. Chem.*, 1977, 30:689-694.
Goussu, C., et al., "Optimized Synthesis of Functionalized Fluorescent Oligodeoxynucleotides for Protein Labeling" *Bioconjugate Chemistry*, 16:465-470 (2005).
Law, et al., "Squaraine chemistry. On the anomalous mass spectra of bis(4-dimethylaminophenyl)squaraine and its derivatives" *Can. J. Chem.*, 64:1607-1619 (1986).
Mujumdar, R.B., et al., "Cyanine Dye Labeling Reagents: Sulfoindocyanine Succinimidyl Esters" *Bioconjugate Chem.*, 4(2):105-111 (Mar./Apr. 1993).
Mujumdar, S.R., et al., "Cyanine Dye Labeling Reagents: Sulfobenzindocyanine Succinimidyl Esters" *Bioconjugate Chem.*, 7:356-362 (1996).
Narayanan, N., et al., "A New Method for the Synthesis of Heptamethine Cyanine Dyes: Synthesis of Near-Infra Red Labels" *J. Org. Chem.*, 60:2391-2395 (1995).
Oswald, B., et al., "Synthesis, Spectral Properties, and Detection Limits of Reactive Squaraine Dyes, a New Class of Diode Laser Compatible Fluorescent Protein Labels" *Bioconj. Chem.*, 10:925-931 (1999).
Oswald, B., et al., "Novel Diode Laser-compatible Fluorophores and Their Application to Single Molecule Detection, Protein Labeling and Fluorescence Resonance Energy Transfer Immunoassay" *Photochemistry and Photobiology*, 74(2):237-245 (2001).
Reddington, M.V., "New Glycoconjugated Cyanine Dyes as Fluorescent Labeling Reagents" *J. Chem. Soc. Perkin Trans.*, 1:143-147 (1998).
Reynolds, G.A., et al., "Stable Heptmethine pyrilium Dyes That Absorb in the Infrared" *J. Org. Chem.*, 42(5):885-888 (1977).
Sharman, W.M., et al., "Novel Water Soluble Phthalocyanines with Phosphonate Moieties on the Benzo Rings" *Tetrahedron Letters* 37(33):5831-5834 (1996).
Tavs, P., *Chem. Ber.*, "Reaction of Aryl Halides with Trialkyl Phosphites and Dialkyl Benzenephosphonites to Aromatic Phosphonates and Phosphinates by Nickel Salt Catalysed Arylation," 103:2428-2436 (1970).

\* cited by examiner

*Primary Examiner*—Mark Staples
(74) *Attorney, Agent, or Firm*—Morgan, Lewis & Bockius, LLP

(57) ABSTRACT

The invention provides a novel class of fluorescent compounds. Also provided are conjugates of the fluorescent compounds, methods of using the fluorescent compounds and their conjugates as well as kits including the fluorescent compounds and their conjugates.

40 Claims, 3 Drawing Sheets

FIGURE 1A

| Compound # | Dye Structure | Absorption Max (nm) | Emission Max (nm) |
|---|---|---|---|
| 9 | | 646 | 663 |
| 11 | | 548 | 563 |
| 13 | | 664 | 683 |
| 15 | | 656 | 745 |
| 20 | | 652 | 670 |
| 21 | | 555 | 568 |

FIGURE 1B

| | | | |
|---|---|---|---|
| 22 | *(structure)* | 651 | 668 |
| 23 | *(structure)* | 554 | 567 |
| 24 | *(structure)* | 635 | 646 |
| 26 | *(structure)* | 628 | 638 |
| 30 | *(structure)* | 649 | 665 |
| 31 | *(structure)* | 552 (520) | 566 |

FIGURE 1C

| 33 | | 786 | 804 |
|---|---|---|---|
| 34 | | 784 | 804 |
| 39 | | 648 | 663 |
| 40 | | 646 | 661 |
| 42 | | 647 | 665 |
| 43 | | 550 | 564 |

WATER SOLUBLE FLUORESCENT COMPOUNDS

BACKGROUND OF THE INVENTION

Fluorescent compounds are widely used as labels in biology and medicine. Through many years of refinement a number of fluorescent compound properties have been found to be advantageous for applications such as protein and antibody labeling. These properties include 1) low non-specific binding, 2) good photostability, 3) ease of chemical modification to permit tuning of absorption and emission wavelengths, 4) good water solubility and 5) resistance to the formation of dimers and higher aggregate. Generally, to achieve the latter two properties, chemical modification of the core fluorescent compound structure is performed to attach charged and neutral water solubilizing residues. Most commonly, electronically charged groups, such as sulfonate (e.g. U.S. Pat. Nos. 5,268,486, and 5,486,616) and quaternary ammonium (e.g. U.S. Pat. No. 6,348,599), have been used to impart water solubility to fluorescent compounds but examples also exist in which neutral groups such as carbohydrates (e.g. U.S. Pat. No. 5,877,310) and polyethylene glycol residues (e.g. Devlin et al, *Clin. Chemistry* 1993, 39, 1939) have been used. Nearly all commercially available biological labels that make use of the charged groups employ the sulfonate group as a water solubilizing substituent. These labels can aggregate and thus reduce label efficacy. There remains a need in the art for improved fluorescent compounds.

SUMMARY OF THE INVENTION

The present invention provides fluorescent compounds comprising a structure according to Formula I:

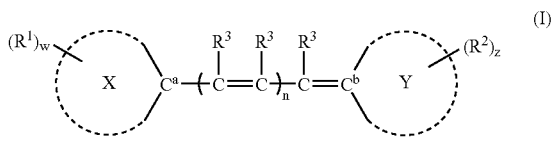

wherein the dotted lines encircling X and Y are each independently selected from atoms necessary for the formation of one ring to three fused rings having 4 to 7 atoms in each ring. At least one atom in the ring comprising $C^a$ is a nitrogen, and at least at least one atom in the ring comprising $C^b$ is a nitrogen. The indices w and z are integers independently selected from 0 to the number of atoms necessary for the formation of X or Y, with the proviso that w and z cannot both be 0. Each $R^3$ is a member independently selected from H, $OR^{30}$, $SR^{30}$, $NR^{30}R^{30}$, halogen, CN, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl and a reactive functional group. Two $R^3$ groups, together with the atoms to which they are attached, can be optionally joined to form a ring. The index n is an integer selected from 0 to 4. $R^1$ and $R^2$ are members independently selected from $R^1$ and $R^2$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, halogen, reactive functional group, $NO_2$, CN, $P(O)(OR^4)(OR^5)$, $D^1R^6$, $NR^7R^8$ and $C(D^2)R^9$, wherein at least one of $R^1$ and $R^2$ is $P(O)(OR^{30})(OR^{30})$. $D^1$ is a member selected from O and S. $D^2$ is a member selected from O, S and NH. $R^4$ and $R^5$ are members independently selected from H, substituted or unsubstituted $C_1$-$C_4$ alkyl, substituted or unsubstituted $C_1$-$C_4$ heteroalkyl. At least one of $R^4$ and $R^5$ is H. $R^6$, $R^7$ and $R^8$ are members independently selected from H, substituted or unsubstituted alkyl and substituted or unsubstituted heteroalkyl. $R^7$ and $R^8$, together with the nitrogen to which they are attached, can be optionally joined to form a member selected from a reactive functional group, —$NHNH_2$, —N=N=N, —N=C=S and —N=C=O. $R^9$ is a member selected from H, substituted or unsubstituted alkyl, substituted or unsubstituted heteroalkyl, a reactive functional group, $NR^{10}R^{11}$ and $OR^2$. $R^{10}$ and $R^{11}$ are members independently selected from H, substituted or unsubstituted alkyl and substituted or unsubstituted heteroalkyl. $R^{12}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl and $C(O)R^{13}$. $R^{13}$ is a member selected from substituted or unsubstituted alkyl and substituted or unsubstituted heteroalkyl. Each $R^{30}$ is independently selected from H, a negative charge and a salt counterion.

The invention also provides methods of making the fluorescent compounds and conjugates, methods of using the fluorescent compounds and their conjugates as well as kits including the fluorescent compounds and their conjugates.

BRIEF DESCRIPTION OF THE DRAWINGS

FIG. 1 provides a representative list of the compounds of the invention.

DETAILED DESCRIPTION OF THE INVENTION

Abbreviations

The abbreviations used herein generally have their conventional meaning within the chemical and biological arts. For example: $Et_3N$, triethylamine; MeOH, methanol; and DMSO, dimethylsulfoxide.

"FET," as used herein, refers to "Fluorescence Energy Transfer."

"FRET," as used herein, refers to "Fluorescence Resonance Energy Transfer." These terms are used herein to refer to both radiative and non-radiative energy transfer processes. For example, processes in which a photon is emitted and those involving long-range electron transfer are included within these terms. Throughout this specification, both of these phenomena are subsumed under the general term "donor-acceptor energy transfer."

Definitions

"Compound of the invention," as used herein refers to the compounds discussed herein, pharmaceutically acceptable salts and prodrugs of these compounds.

The term "poly" as used herein means at least 2. For example, a polyvalent metal ion is a metal ion having a valency of at least 2.

"Moiety" refers to the radical of a molecule that is attached to another moiety.

The symbol ⌇, whether utilized as a bond or displayed perpendicular to a bond, indicates the point at which the displayed moiety is attached to the remainder of the molecule.

As used herein, "nucleic acid" means any natural or non-natural nucleoside, or nucleotide and oligomers and polymers thereof, e.g., DNA, RNA, single-stranded, double-stranded, triple-stranded or more highly aggregated hybridization motifs, and any chemical modifications thereof. Modifications include, but are not limited to, conjugation with a compound of the invention or a construct that includes a compound of the invention covalently attached to a linker that tethers the compound to the nucleic acid, and those providing the nucleic acid with a group that incorporates additional charge, polarizability, hydrogen bonding, electrostatic interaction, fluxionality or functionality to the nucleic acid. Exemplary modifications include the attachment to the nucleic acid, at any position, of one or more hydrophobic or hydrophilic moieties, minor groove binders, intercalating agents, quenchers, chelating agents, metal chelates, solid supports, and other groups that are usefully attached to nucleic acids.

Exemplary modified nucleic acids include, but are not limited to, peptide nucleic acids (PNAs), those with phosphodiester group modifications (e.g., replacement of $O^-$ with OR, NR, or SR), 2'-, 3'- and 5'-position sugar modifications, modifications to the base moiety, e.g., 5-position pyrimidine modifications, 8-position purine modifications, modifications at exocyclic amines, substitution of 4-thiouridine, substitution of 5-bromo or 5-iodo-uracil; backbone modifications, i.e., substitution of a phosphodiester bridge ($P(O)O_3$) with another moiety, methylations, unusual base-pairing combinations such as the isobases, isocytidine and isoguanidine and the like. Nucleic acids can also include non-natural bases, e.g., nitroindole. Non-natural bases include bases that are modified with a compound of the invention or a linker-compound of the invention construct, a minor groove binder, an intercalating agent, a hybridization enhancer, a chelating agent, a metal chelate, a quencher, a fluorophore, a fluorogenic compound, etc. Modifications within the scope of "nucleic acid" also include 3' and 5' modifications with one or more of the species described above.

"Nucleic acid" also includes species that are modified at one or more internucleotide bridge (e.g., $P(O)O_3$) by replacing or derivatizing an oxygen of the bridge atom with a compound of the invention or a species that includes a compound of the invention attached to a linker. For example, "nucleic acid" also refers to species in which the $P(O)O_3$ moiety of a natural nucleic acid is replaced with a non-natural internucleotide bridge species, e.g., —ORP(O)O—, —ROP(O)R—, —ORP(O)OR——ROP(O)OR—or —RP(O)R—in which the symbol "-" indicates the position of attachment of the bridge to the 2'-, 3'- or 5'-carbon (or the oxygen pendant from this carbon) of a nucleotide sugar moiety, thus allowing the placement of the exemplified, and other, non-natural linkers between adjacent nucleoside sugar moieties. Exemplary linker subunits ("R") include substituted or unsubstituted alkyl and substituted or unsubstituted heteroalkyl moieties. "R" can include a compound of the invention or a construct of a linker and a compound of the invention.

Furthermore, "nucleic acid" includes those species in which one or more internucleotide bridge does not include phosphorus: the bridge being optionally modified with a compound of the invention or a linker arm-xanthene fluorescent compound construct. An exemplary bridge includes a substituted or unsubstituted alkyl or substituted or unsubstituted heteroalkyl moiety in which a carbon atom is the locus for the interconnection of two nucleoside sugar residues (or linker moieties attached thereto) and a compound of the invention or a linker construct that includes a compound of the invention. The discussion above is not limited to moieties that include a carbon atom as the point of attachment; the locus can also be another appropriate linking atom, such as nitrogen or another atom.

Those of skill in the art will understand that in each of the "nucleic acid" compounds described above, the structure corresponding to the term "compound of the invention" can be interchanged with a quencher, a hybridization enhancer, and intercalator, a minor groove binder, a chelating agent, a metal chelate or other moiety that is usefully conjugated to a nucleic acid, optionally being present in tandem with species that include a compound of the invention or a derivative thereof.

As used herein, "quenching group" refers to any fluorescence-modifying group of the invention that can attenuate at least partly the light emitted by a fluorescent group. This attenuation is referred to herein as "quenching". Hence, illumination of the fluorescent group in the presence of the quenching group leads to an emission signal that is less intense than expected, or even completely absent. Quenching typically occurs through energy transfer between the fluorescent group and the quenching group.

The term "amino acid" refers to naturally occurring and synthetic amino acids, as well as amino acid analogs and amino acid mimetics. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

"Peptide" refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

"Bioactive species," refers to molecules that, when administered to an organism, affect that organism. Exemplary bioactive species include pharmaceuticals, pesticides, herbicides, growth regulators and the like. Bioactive species encompasses small molecules (i.e., approximately <1000 daltons), oligomers, polymers and the like. Also included are nucleic acids and their analogues, peptides and their analogues and the like.

"Carrier molecule," as used herein refers to any molecule to which a compound of the invention is attached. Representative carrier molecules include a protein (e.g., enzyme, antibody), glycoprotein, peptide, saccharide (e.g., mono- oliogo- and poly-saccharides), hormone, receptor, antigen, substrate, metabolite, transition state analog, cofactor, inhibitor, drug, fluorescent compound, nutrient, growth factor, etc., without limitation. "Carrier molecule" also refers to species that might not be considered to fall within the classical definition of "a molecule," e.g., solid support (e.g., synthesis support, chromatographic support, membrane), virus and microorganism.

"Activated derivatives of hydroxyl moieties," and equivalent species, refer to compounds in which an oxygen-containing leaving group is formally derived from a hydroxyl moiety.

"Activated derivatives of carboxyl moieties," and equivalent species, refer to compounds in which an oxygen-containing leaving group is formally derived from a carboxyl moiety.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include mono-, di- and multivalent radicals, having the number of carbon atoms designated (i.e. $C_1$-$C_{10}$ means one to ten carbons). Examples of saturated alkyl radicals include, but are not limited to, groups such as methyl, methylene, ethyl, ethylene, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, includes "alkylene" and those derivatives of alkyl defined in more detail below, such as "heteroalkyl." Alkyl groups, which are limited to hydrocarbon groups, are termed "homoalkyl".

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Also included are di- and multi-valent species such as "cycloalkylene." Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, species such as trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Also included are di- and multi-valent linker species, such as "arylene." Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) ("alkyl group substituents") can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR'—C(O)(NR'R"R''')=NR"", —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups ("aryl group substituents") are varied and are selected from, for example: halogen, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R"" are preferably independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a compound of the invention includes more than one R group, for example, each of the R groups is independently selected as are each R', R", R''' and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

"Analyte," "target," "substance to be assayed", and "target species," as utilized herein refer to the species of interest in an assay mixture. The terms refer to a substance, which is detected qualitatively or quantitatively using a material, process or device of the present invention. Examples of such substances include cells and portions thereof, enzymes, antibodies, antibody fragments and other biomolecules, e.g., antigens, polypeptides, glycoproteins, polysaccharides, complex glycolipids, nucleic acids, effector molecules, receptor molecules, enzymes, inhibitors and the like and drugs, pesticides, herbicides, agents of war and other bioactive agents.

More illustratively, such substances include, but are not limited to, tumor markers such as a-fetoprotein, carcinoembryonic antigen (CEA), CA 125, CA 19-9 and the like; various proteins, glycoproteins and complex glycolipids such as β$_2$-microglobulin (β$_2$m), ferritin and the like; various hormones such as estradiol (E$_2$), estriol (E$_3$), human chorionic gonadotropin (hCG),uteinizing hormone (LH), human placental lactogen (hPL) and the like; various virus-related antigens and virus-related antibody molecules such as HBs antigen, anti-HBs antibody, HBc antigen, anti-HBc antibody, anti-HCV antibody, anti-HIV antibody and the like; various allergens and their corresponding IgE antibody molecules; narcotic drugs and medical drugs and metabolic products thereof; and nucleic acids having virus- and tumor-related polynucleotide sequences.

The term, "assay mixture," refers to a mixture that includes the analyte and other components. The other components are, for example, diluents, buffers, detergents, and contaminating species, debris and the like that are found mixed with the target. Illustrative examples include urine, sera, blood plasma, total blood, saliva, tear fluid, cerebrospinal fluid, secretory fluids from nipples and the like. Also included are solid, gel or sol substances such as mucus, body tissues, cells and the like suspended or dissolved in liquid materials such as buffers, extractants, solvents and the like.

The term "drug" or "pharmaceutical agent," refers to bioactive compounds that cause an effect in a biological organism. Drugs used as affinity moieties or targets can be neutral or in their salt forms. Moreover, the compounds can be used in the present method in a prodrug form. Prodrugs are those compounds that readily undergo chemical changes under physiological conditions to provide the compounds of interest in the present invention.

"Ring" as used herein means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 to 7 atoms in the encircling arrangement. The ring optionally included a heteroatom. Thus, the term "5- to 7-membered ring" includes, for example pyridinyl and piperidinyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), aluminum (Al) and boron (B).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The term "salt counterion" is meant to include salts of the compounds of the invention which are prepared with relatively nontoxic acids or bases, depending on the particular substituents found on the compounds described herein. When compounds of the present invention contain relatively acidic fuictionalities, base addition salts can be obtained by contacting the neutral form of such compounds with a sufficient amount of the desired base, either neat or in a suitable inert solvent. Examples of salt counterions include sodium, potassium, calcium, ammonium, quaternary alkyl amino, organic amino, or magnesium salt, or a similar salt.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

DESCRIPTION OF THE EMBODIMENTS

Introduction

In contrast to the sulfonate group, the phosphonate group is diprotic and therefore can carry two negative charges under certain pH ranges. As such it can offer greater resistance to aggregation. The fluorescent compounds of the present invention make use of the phosphonate group to impart water solubility and resistance to aggregation. Specifically. by attaching the phosphonate group directly to the aromatic residues of the fluorescent compound, resistance to aggregation is achieved resulting in highly fluorescent water soluble compounds that are suitable for use as fluorescent labels.

I. The Compounds

In a first aspect, the invention provides a fluorescent compound comprising a structure according to Formula I:

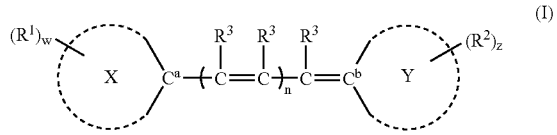

wherein the dotted lines encircling X and Y are each independently selected from atoms necessary for the formation of one ring to three fused rings having 4 to 7 atoms in each ring. At least one atom in the ring comprising $C^a$ is a nitrogen, and at least at least one atom in the ring comprising $C^b$ is a nitrogen. The indices w and z are integers independently selected from 0 to the number of atoms necessary for the formation of X or Y, with the proviso that w and z cannot both be 0. Each $R^3$ is a member independently selected from H, $OR^{30}$, $SR^{30}$, $NR^{30}R^{30}$, halogen, CN, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl and a reactive functional group. Two $R^3$ groups, together with the atoms to which they are attached, can be optionally joined to form a ring. The index n is an integer selected from 0 to 4. $R^1$ and $R^2$ are members independently selected from $R^1$ and $R^2$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, halogen, reactive finctional group, $NO_2$, CN, $P(O)(OR^4)(OR^5)$, $D^1R^6$, $NR^7R^8$ and $C(D^2)R^9$, wherein at least one of $R^1$ and $R^2$ is $P(O)(OR^{30})(OR^{30})$. $D^1$ is a member selected from O and S. $D^2$ is a member selected from O, S and NH. $R^4$ and $R^5$ are members independently selected from H, substituted or unsubstituted $C_1$-$C_4$ alkyl, substituted or unsubstituted $C_1$-$C_4$ heteroalkyl. At least one of $R^4$ and $R^5$ is H. $R^6$, $R^7$ and $R^8$ are members independently selected from H, substituted or unsubstituted alkyl and substituted or unsubstituted heteroalkyl. $R^7$ and $R^8$, together with the nitrogen to which they are attached, can be optionally joined to form a member selected from a reactive functional group, —$NHNH_2$, —N=N=N, —N=C=S and —N=C=O. $R^9$ is a member selected from H, substituted or unsubstituted alkyl, substituted or unsubstituted heteroalkyl, a reactive functional group, $NR^{10}OR^{11}$ and $OR^{12}$. $R^{10}$ and $R^{11}$ are members independently selected from H, substituted or unsubstituted alkyl and substituted or unsubstituted heteroalkyl. $R^{12}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl and $C(O)R^{13}$. $R^{13}$ is a member selected from substituted or unsubstituted alkyl and substituted or unsubstituted heteroalkyl. Each $R^{30}$ is independently selected from H, a negative charge and a salt counterion.

In an exemplary embodiment, said one to three fused rings have 5 to 6 atoms in each ring. In another exemplary embodiment, said one to three fused rings are each unsaturated. In another exemplary embodiment, said one to three fused rings are each aromatic. In another exemplary embodiment, at least one of $R^1$ and $R^2$ is P(O)(OH)(OH). In an exemplary embodiment,

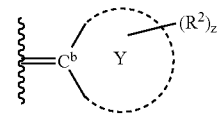

has a structure according to

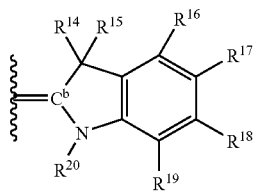

wherein $R^{14}$ and $R^{15}$ are members independently selected from H, substituted or unsubstituted alkyl, substituted or unsubstituted heteroalkyl, substituted or unsubstituted cycloalkyl and substituted or unsubstituted heterocycloalkyl. $R^{16}$, $R^{17}$, $R^{18}$, $R^{19}$ and $R^{20}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl, halogen, reactive functional group, $NO_2$, CN, $P(O)(OR^4)(OR^5)$, $D^1R^6$, $NR^7R^8$, and $C(D^2)R^9$, wherein at least one of $R^{16}$, $R^{17}$, $R^{18}$ and $R^{19}$ is $P(O)(OR^{30})(OR^{30})$. $D^1$ is a member selected from O and S. $D^2$ is a member selected from O, S and NH. $R^4$ and $R^5$ are members independently selected from H, substituted or unsubstituted $C_1$-$C_4$ alkyl, substituted or unsubstituted $C_1$-$C_4$ heteroalkyl. At least one of $R^4$ and $R^5$ is H. $R^6$, $R^7$ and $R^8$ are members independently selected from H, substituted or unsubstituted alkyl, substituted or unsubstituted heteroalkyl and a reactive functional group. $R^7$ and $R^8$, together with the nitrogen to which they are attached, can be optionally joined to form a member selected from a reactive functional group, —$NHNH_2$, —N=N=N, —N=C=S and —N=C=O. $R^9$ is a member selected from H, substituted or unsubstituted alkyl, substituted or unsubstituted heteroalkyl, $NR^{10}R^{11}$ and $OR^{12}$. $R^{10}$ and $R^{11}$ are members independently selected from H, substituted or unsubstituted alkyl and substituted or unsubstituted heteroalkyl. $R^{12}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl and C(O)$R^{13}$. $R^{13}$ is a member selected from substituted or unsubstituted alkyl and substituted or unsubstituted heteroalkyl.

In another exemplary embodiment, either a) $R^1$ and $R^{20}$ are independently selected from substituted or unsubstituted alkyl; or b) at least one of said $R^1$ and $R^{20}$ further comprises a member selected from a reactive functional group, solid support and carrier molecule.

In another exemplary embodiment, the fluorescent compound has a structure which is a member selected from

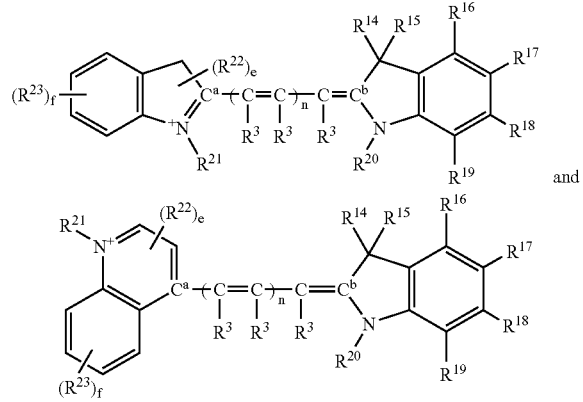

in which the index e is an integer selected from 1 to 2, and the index f is an integer selected from 1 to 4. $R^{20}$ and $R^{21}$ are members independently selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; with the proviso that either a) $R^{20}$ and $R^{21}$ are independently selected from substituted or unsubstituted alkyl; or b) at least one of said $R^{20}$ and $R^{21}$ further comprises a member selected from an oxygen containing reactive functional group, solid support and carrier molecule. $R^{22}$ and $R^{23}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl, halogen, reactive functional group, $NO_2$, CN, $P(O)(OR^4)(OR^5)$, $D^1R^6$, $NR^7R^8$, and $C(D^2)R^9$, wherein at least one of $R^{16}$, $R^{17}$, $R^{18}$, $R^{19}$, $R^{20}$, $R^{23}$ and $R^{24}$ is $P(O)(OR^{30})(OR^{30})$. $D^1$ is a member selected from O and S. $D^2$ is a member selected from O, S and NH. $R^4$ and $R^5$ are members independently selected from H, substituted or unsubstituted $C_1$-$C_4$ alkyl, substituted or unsubstituted $C_1$-$C_4$ heteroalkyl, wherein at least one of $R^4$ and $R^5$ is H. $R^6$, $R^7$ and $R^8$ are members independently selected from H, substituted or unsubstituted alkyl and substituted or unsubstituted heteroalkyl wherein $R^7$ and $R^8$, together with the nitrogen to which they are attached, can be optionally joined to form a member selected from a reactive functional group, —$NHNH_2$, —N=N=N, —N=C=S and —N=C=O. $R^9$ is a member selected from H, substituted or unsubstituted alkyl, substituted or unsubstituted heteroalkyl, $NR^{10}R^{11}$ and $OR^{12}$ wherein $R^{10}$ and $R^{11}$ are members independently selected from H, substituted or unsubstituted alkyl and substituted or unsubstituted heteroalkyl. $R^{12}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl and C(O)$R^{13}$. $R^{13}$ is a member selected from substituted or unsubstituted alkyl and substituted or unsubstituted heteroalkyl.

In another exemplary embodiment, $R^{17}$ is $P(O)(OR^{30})(OR^{30})$. In another exemplary embodiment, $R^{14}$ and $R^{15}$ are members independently selected from substituted or unsubstituted $C_1$-$C_4$ alkyl. In another exemplary embodiment, $R^1$ or $R^2$ is a member selected from

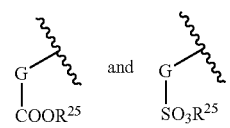

wherein G is a member selected from substituted or unsubstituted alkyl and substituted or unsubstituted aryl and $R^{25}$ is a member selected from H, a negative charge, a salt counterion, reactive finctional group, substituted or unsubstituted alkyl and substituted or unsubstituted heteroalkyl.

In yet another exemplary embodiment, the fluorescent compound is a member selected from

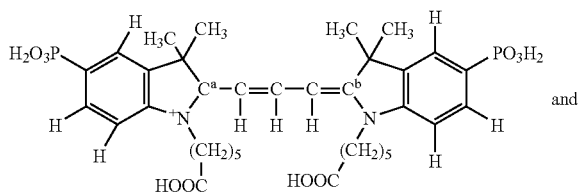

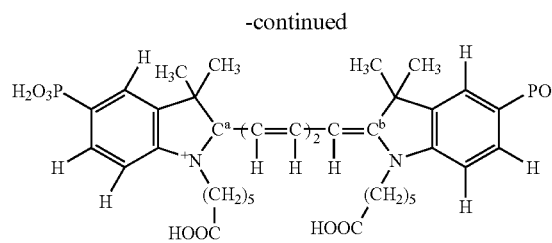

In another exemplary embodiment, $R^{20}$ is substituted or unsubstituted $C_1$-$C_4$ alkyl. In another exemplary embodiment, the fluorescent compound is a member selected from

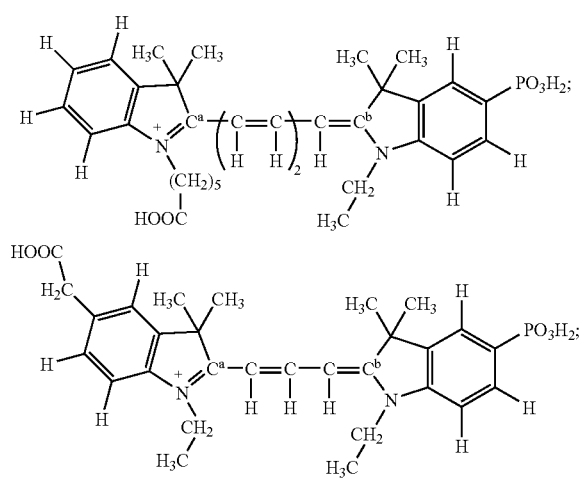

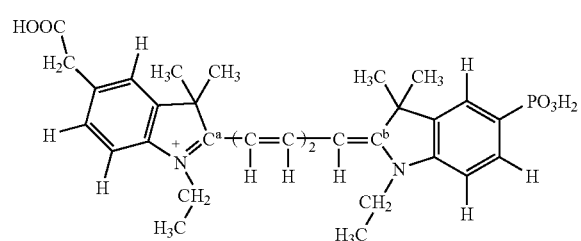

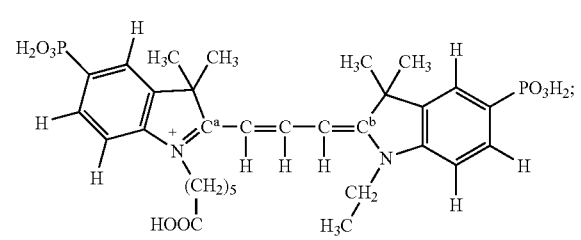

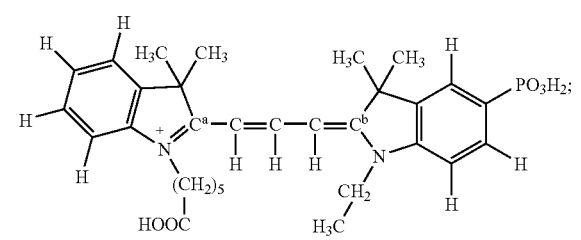

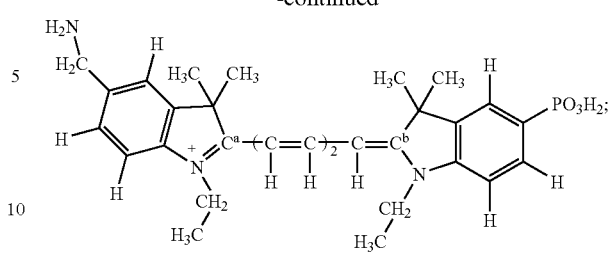

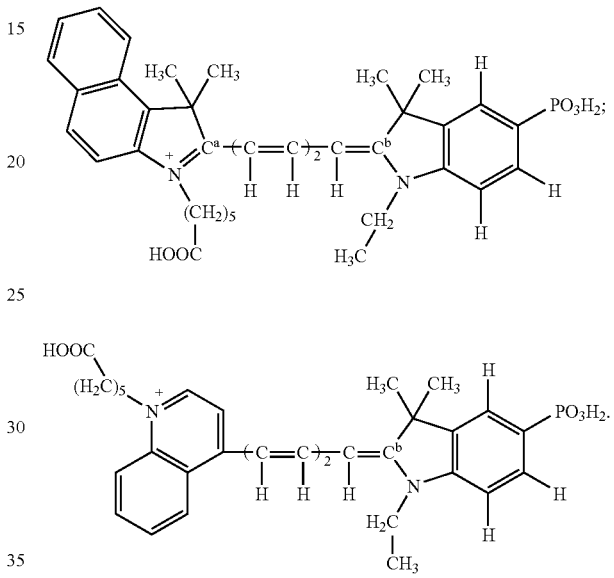

In yet another exemplary embodiment, $-(C(R^3)=C(R^3))_n-C(R^3)=$ is a member selected from:

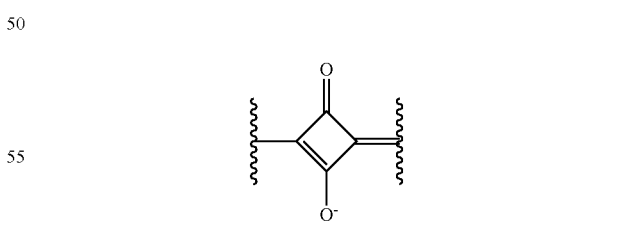

wherein $Z^4$ is a member selected from H, $OR^{30}$, $SR^{30}$, $NR^{30}R^{30}$, halogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In another exemplary embodiment, the fluorescent compound is a member selected from

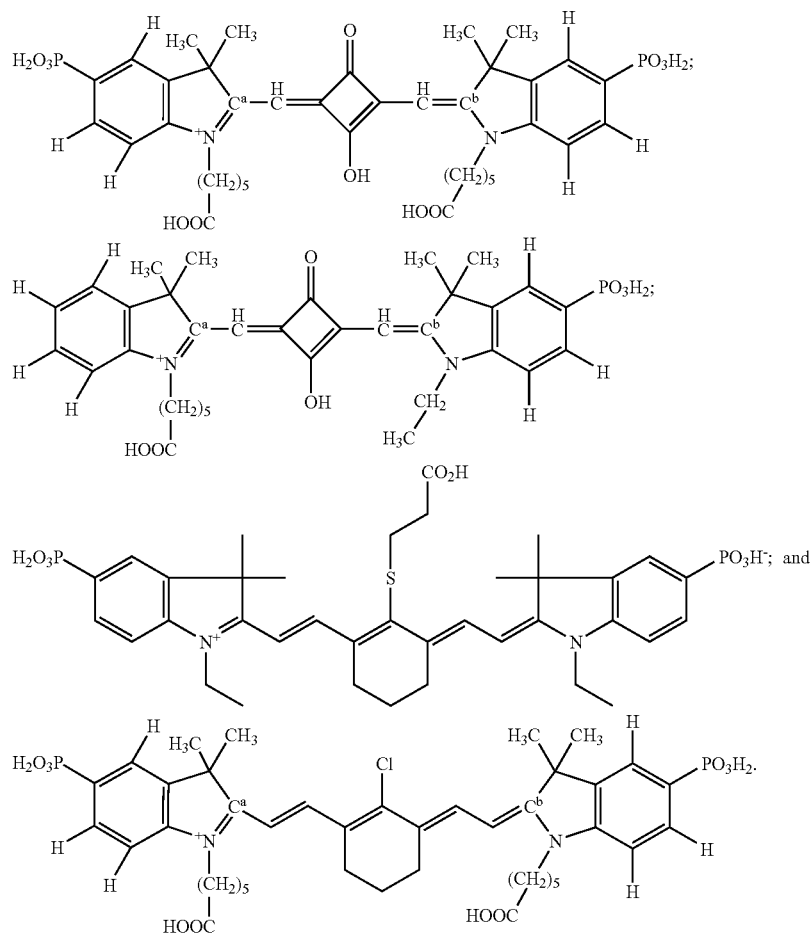
In another exemplary embodiment, the fluorescent compound is a member selected from
In another exemplary embodiment, the fluorescent compound is a member selected from
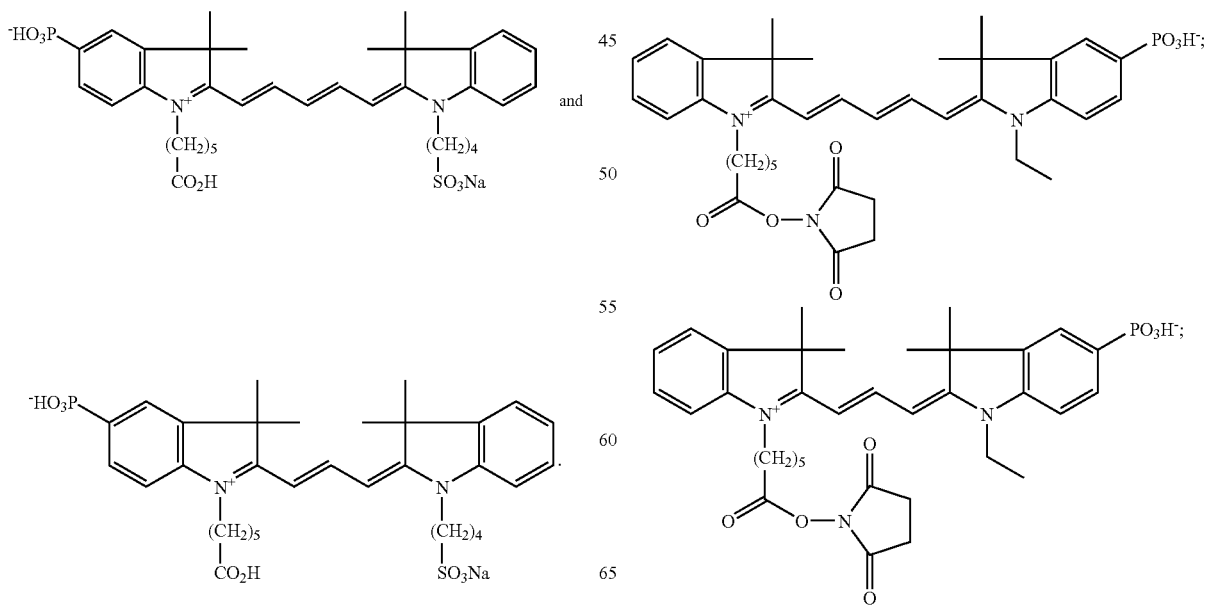

-continued

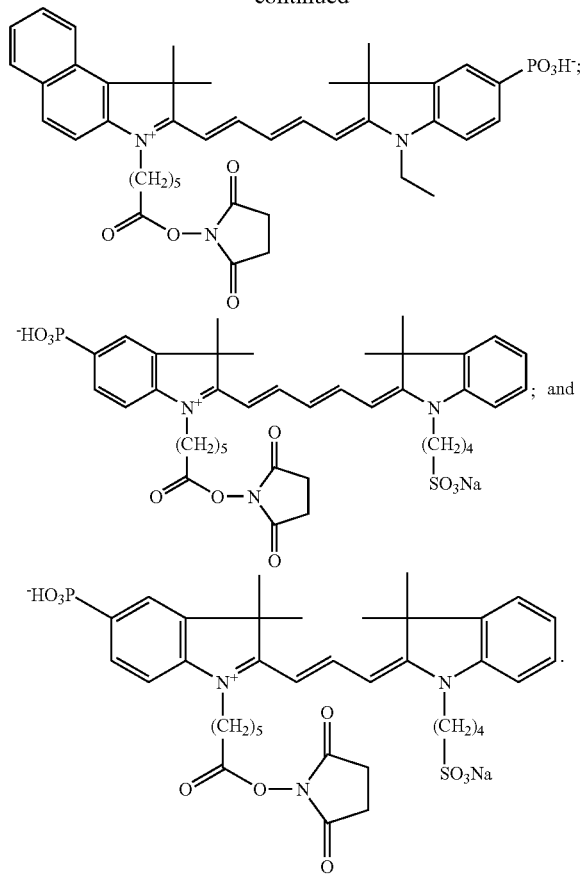

In another exemplary embodiment, at least one of said $R^1$ and $R^{20}$ further comprises —$NR^{35}R^{36}$, wherein $R^{35}$ and $R^{36}$ are members independently selected from substituted or unsubstituted alkyl, substituted or unsubstituted heteroalkyl, substituted or unsubstituted heterocycloalkyl, substituted or unsubstituted aryl and substituted or unsubstituted heteroaryl, and $R^{35}$ and $R^{36}$, together with the nitrogen to which they are bound, are optionally joined to form a ring system.

In another exemplary embodiment, the carrier molecule further comprises a quencher moiety. In another exemplary embodiment, the fluorescent compound, together with said quencher moiety, comprise a donor-acceptor energy transfer pair. In another exemplary embodiment, the quencher moiety has substantially no native fluorescence. In another exemplary embodiment, the quencher moiety comprises at least three residues, wherein each of said residues is independently selected from substituted or unsubstituted aryl and substituted or unsubstituted heteroaryl. In addition, at least two of said residues are covalently linked via an exocyclic diazo bond. In another exemplary embodiment, the fluorescent compound is attached to a nucleic acid at a position which is a member selected from the 3'-terminus, the 5'-terminus, a nucleobase, and a phosphorus-containing internucleotide bridge of said nucleic acid. In another exemplary embodiment, the nucleic acid further comprises a probe which is a member selected from a molecular beacon, scorpion probe, sunrise probe, conformationally assisted probe and Taq-Man™ probe. In yet another exemplary embodiment, the carrier molecule is a peptide comprising a cleavage recognition site for an enzyme. In another exemplary embodiment, the enzyme is a member selected from protease, trypsin, enterokinase, HIV-1 protease, prohormone convertase, interleukin-1b-converting enzyme, adenovirus endopeptidase, cytomegalovirus assemblin, leishmanolysin, β-secretase for amyloid precursor protein, thrombin, renin, angiotensin-converting enzyme, cathepsin-D and a kininogenase. In another exemplary embodiment, the fluorescent compound further comprises a member selected from a protein, saccharide, nucleotide monophosphate, nucleotide diphosphate and nucleotide triphosphate. In an exemplary embodiment, the nucleotide monophosphate, diphosphate, or triphosphate can be incorporated into an oligonucleotide. In another exemplary embodiment, the protein is an antibody. In another exemplary embodiment, the saccharide is dextran.

In another exemplary embodiment, in which a member selected from $R^1$ and $R^{20}$ of the fluorescent compound has the formula:

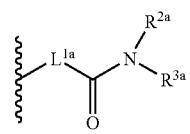

wherein $L^{1a}$ is a member selected from substituted or unsubstituted alkyl and substituted or unsubstituted heteroalkyl. $R^{2a}$ and $R^{3a}$ are members independently selected from H, substituted or unsubstituted alkyl and substituted or unsubstituted heteroalkyl. $R^{2a}$ and $R^{3a}$, together with the nitrogen to which they are attached, are optionally joined to form a ring which is a member selected from substituted or unsubstituted 5-7 membered cycloalkyl and substituted or unsubstituted 5-7 membered heterocycloalkyl. In another exemplary embodiment, $L^{1a}$ does not comprise a carboxylic acid ester.

In another aspect, the invention provides a fluorescent compound having the formula:

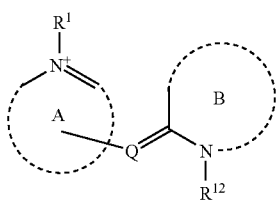

in which ring systems A and B are members independently selected from substituted or unsubstituted aryl and substituted or unsubstituted heteroaryl. At least one of ring systems A and B comprise a substituent, and said substituent is $PO_3H_2$. $R^1$ is a member selected from substituted or unsubstituted alkyl, substituted or unsubstituted heteroalkyl, substituted or unsubstituted heterocycloalkyl, substituted or unsubstituted aryl, substituted or unsubstituted heteroaryl and $COOR^{20}$. $R^{20}$ is a member selected from substituted or unsubstituted alkyl. $R^{12}$ is a member selected from substituted or unsubstituted alkyl and substituted or unsubstituted heteroalkyl. Q is a member selected from substituted or unsubstituted unsaturated alkyl, substituted or unsubstituted unsaturated cycloalkyl, substituted or unsubstituted unsaturated heteroalkyl, and substituted or unsubstituted unsaturated heterocycloalkyl.

Representative compounds according to Formula I are set forth in FIG. 1.

Also within the scope of the present invention are compounds of the invention that are poly- or multi-valent species, including, for example, species such as dimers, trimers, tetramers and higher homologs of the compounds of the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or a reactive analogue thereof, can be attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of the invention). Moreover, the framework can be derivatized with a single species of the invention or more than one species of the invention.

Moreover, the present invention includes compounds within the motif set forth in Formula I, which are functionalized to afford compounds having water-solubility that is enhanced relative to analogous compounds that are not similarly functionalized. Thus, any of the substituents set forth herein can be replaced with analogous radicals that have enhanced water solubility. In a preferred embodiment, additional water solubility is imparted by substitution at a site not essential for the activity of the compounds set forth herein with a moiety that enhances the water solubility of the parent compounds. Methods of enhancing the water-solubility of organic compounds are known in the art. Such methods include, but are not limited to, finctionalizing an organic nucleus with a permanently charged moiety, e.g., quaternary ammonium, sulfonate or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. POLYMERIC DRUGS AND DRUG DELIVERY SYSTEMS, ACS Symposium Series Vol. 469, American Chemical Society, Washington, D.C. 1991.

I.a. Reactive Functional Groups

Certain of the compounds of the invention bear a reactive functional group, such as a component of a linker arm, which can be located at any position on any aryl nucleus or on a chain, such as an alkyl chain, attached to an aryl nucleus, or on the backbone of the chelating agent. In an exemplary embodiment, $R^1$, $R^2$, $R^3$, $R^{14}$, $R^{15}$, $R^{16}$, $R^{17}$, $R^{18}$, $R^{19}$, $R^{20}$, $R^{21}$, $R^{22}$, $R^{23}$ or $R^{25}$ has a reactive functional group. When the reactive finctional group is attached to an alkyl, or substituted alkyl chain tethered to an aryl nucleus, the reactive group is preferably located at a terminal position of an alkyl chain. Reactive functional groups and classes of reactions useful in practicing the present invention are generally those that are well known in the art of bioconjugate chemistry. Currently favored classes of reactions available with reactive functional groups of the invention are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups, which can be converted to esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds; and (k) phosphoramidites and other standard functional groups useful in nucleic acid synthesis.

In an exemplary embodiment, the reactive functional groups are members selected from

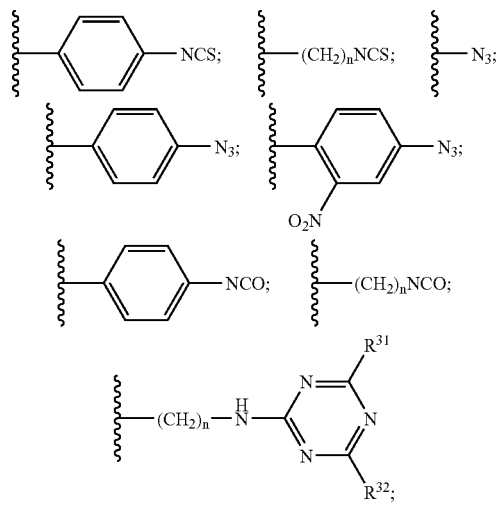

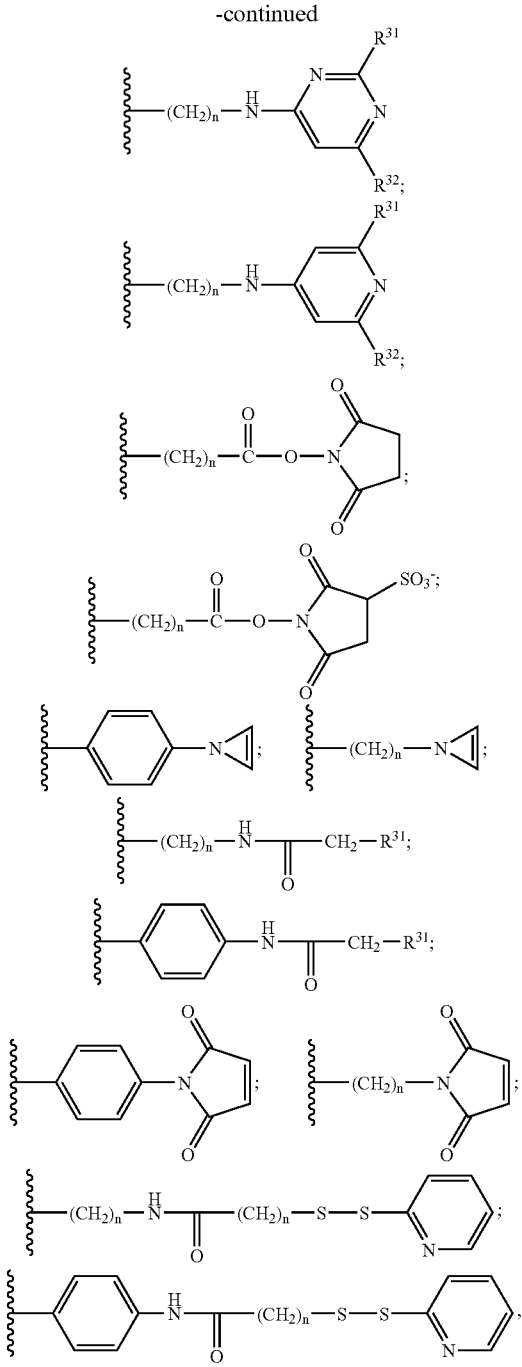

wherein $R^{31}$ and $R^{32}$ are members independently selected from substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

In an exemplary embodiment, the reactive functional groups can react with a corresponding functional group on a target molecule, or the same fluorescent compound, in order to create a fluorescent molecule. These target molecules can be polymers or biomolecules, which include, but are not limited to the group consisting of antibody, ipid, protein, peptide, carbohydrate, nucleotides which contain or are derivatized to contain one or more of an amino, sulphydryl, carbonyl, hydroxyl and carboxyl, phosphate and thiophosphate groups, and oxy or deoxy polynucleic acids which contain or are derivatized to contain one or more of an amino, sulphydryl, carbonyl, hydroxyl and carboxyl, phosphate and thiophosphate groups, microbial materials, drugs, toxins, particles, plastics or glass surfaces and polymers. Reactive functional groups, as well as the corresponding functional groups with which they react, are provided in the following table:

TABLE 1

Possible Reactive Substituents and Sites Reactive Therewith

| Reactive Functional Groups | Corresponding Functional Groups |
|---|---|
| Succinimidyl esters | primary amino, secondary amino, hydroxyl |
| Anhydrides | primary amino, secondary amino, hydroxyl |
| Acyl azides | primary amino, secondary amino |
| Isothiocyanates, isocyanates | amino, thiol, hydroxyl |
| sulfonyl chlorides sulfonyl fluorides | amino, hydroxyl |
| hydrazines, substituted hydrazines | aldehydes, ketones |
| hydroxylamines, substituted hydroxylamines | amino, hydroxyl |
| acid halides | amino, hydroxyl |
| haloacetamides, maleimides | thiol, imidazoles, hydroxyl, amino |
| carbodiimides | carboxyl groups |
| phosphoramidites | hydroxyl |
| azides | alkynes |

For example, in order to attach a compound of the invention to the hydroxyl moiety on a serine amino acid, exemplary reactive functional groups include, succinimidyl esters, anhydrides, isothiocyantes, thiocyanates, sulfonyl chlorides, sulfonyl fluorides, acid halides, haloacetamides, maleimides and phosphoramidites.

The reactive functional groups can be chosen such that they do not participate in, or interfere with, the reactions necessary to assemble the compound of the invention. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

II. Preparation of the Compounds

Compounds of the present invention can be prepared using readily available starting materials or known intermediates. The synthetic schemes set forth below provide exemplary synthetic pathways for the preparation of compounds of the invention.

II.a. General Procedure for Synthesizing Fluorescent Compounds

The fluorescent labels of the invention can be synthesized by one of several routes. One route was found particularly convenient to implement. A heterocyclic structure, such as an indole or a quinoline, containing a substitutable group, such as halide, can be prepared and then alkylated to form a salt. Reaction of the salt with a suitable phosphorylating reagent replaces the substitutable group with a phosphorus containing moiety and in so doing attaches the phosphorus directly to the aromatic ring of the heterocycle. The phosphorus containing heterocyclic salts may then be combined through reaction with an unsaturated linker to other heterocyclic salts to form the fluorescent compound such as a cyanine or a squarane.

The second heterocycle may or may not contain a phosphorus group. Other functional groups may be attached to the fluorescent compound, either directly on the aromatic residues of the heterocycle or through linkers, either before or after fluorescent compound formation. In such a way carboxylic acids, which can be converted to succinimidyl esters with TSTU, amines, sulfonates and other groups can be included to provide chemical reactivity for substrate labeling and additional water solubility.

Investigation of the nickel catalyzed phosphonation reaction demonstrated that the bromoindole 2 could be phosphonated. Further investigation indicated that the indolium salts 3 and 17 could also be phosphonated, to generate phosphonate esters 4 and 5, which could be hydrolyzed to produces the indolium salts 6 and 19, respectively. These salts were used in combination with other indolium, benzindolium and lepidinium salts to synthesize symmetrical and unsymmetrical trimethine, pentamethine and heptamethine fluorescent compounds and also symmetrical and unsymmetrical squarane fluorescent compounds as outlined in the schemes below. Carboxylic acid containing fluorescent compounds were treated with TSTU to prepare N-hydroxysuccinimidyl esters which were then used to label proteins and oligonucleotides.

Fluorescent compounds 9 and 11 can be synthesized according to the synthesis outlined in Scheme 1.

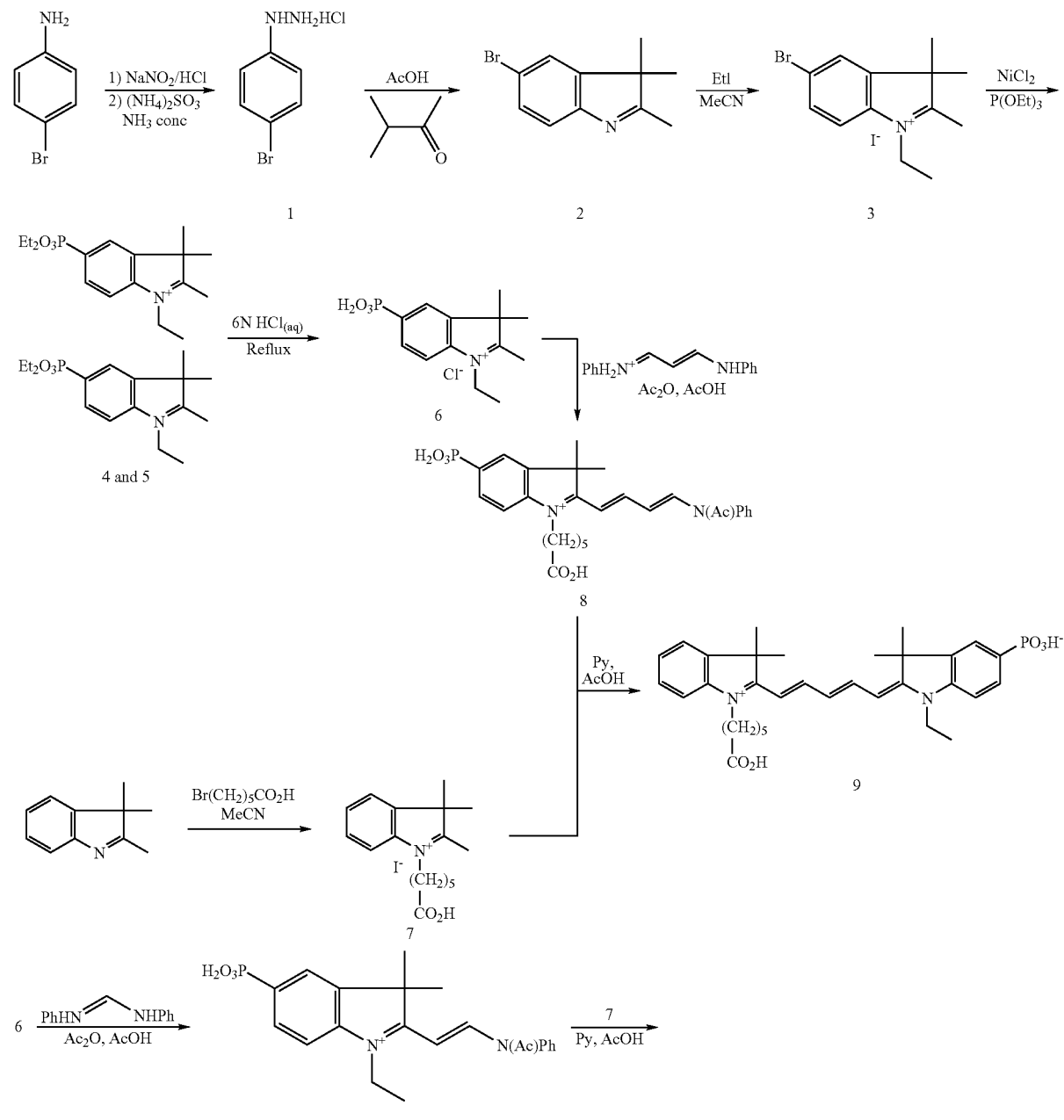

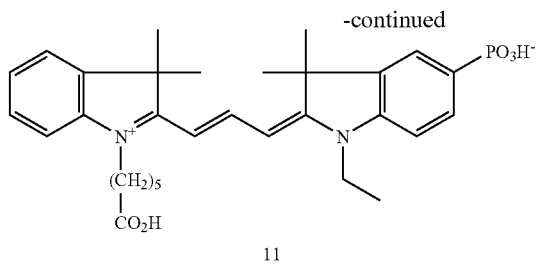

11

In Scheme 1, p-bromophenylhydrazine 1 is reacted with a methylbutanone in acetic acid to form bromoindole 2. Compound 2 is then reacted with ethyl iodide in acetonitrile to form indolium salt 3. Compound 3 is then reacted with nickel chloride and triethylphosphite to produce a mixture of compounds 4 and 5 from which compound 4 was isolated by distillation. Compound 5 is hydrolyzed with refluxing 6 M hydrochloric acid to form compound 6.

Reaction of trimethylindolenine with bromohexanoic acid in acetonitrile produces indolium salt 7. Treatment of 7 with malonaldehyde dianil produces compound 8. Reaction of compound 8 with indolium salt 6 in pyridine and acetic acid forms fluorescent compound 9.

Alternatively, indolium salt 6 can be reacted with diphenylformamidine in order to form compound 10, which is then reacted with compound 7 in pyridine and acetic acid to form fluorescent compound 11.

Fluorescent compounds 13 and 15 can be synthesized according to the synthesis outlined in Scheme 2.

Scheme 2

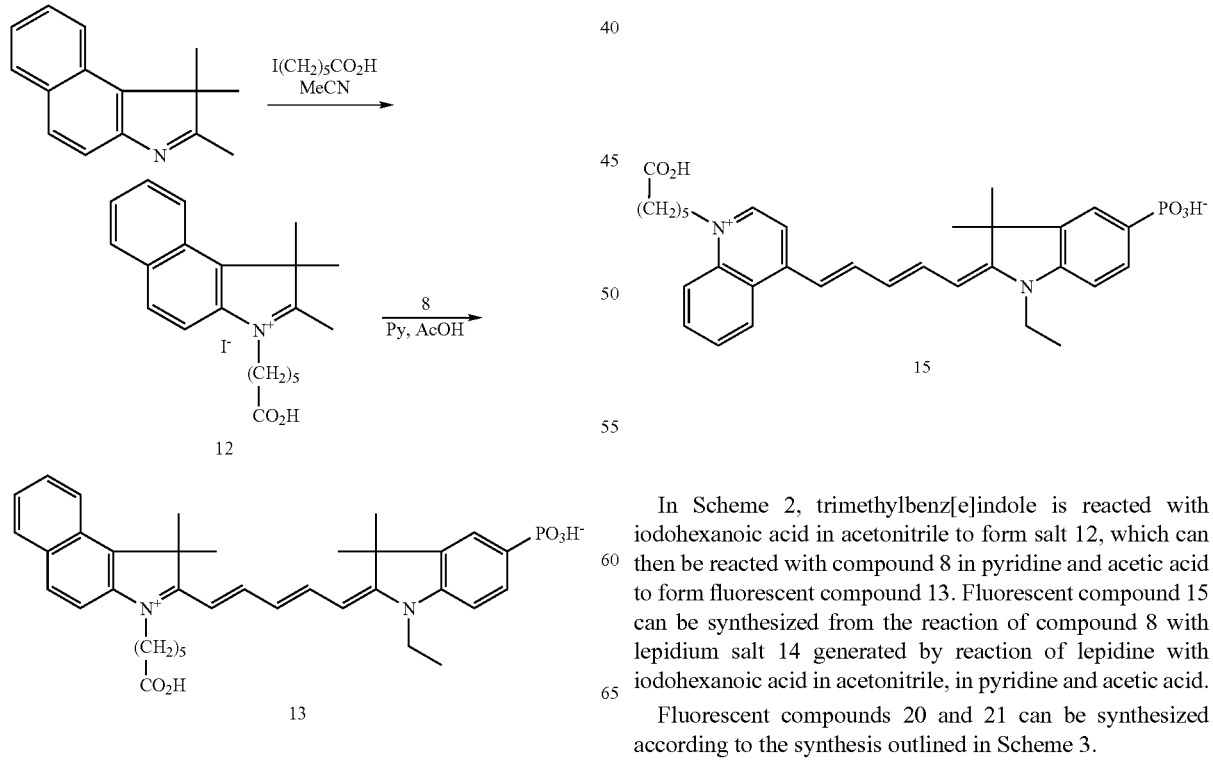

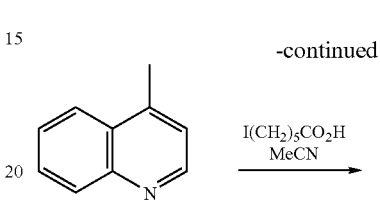

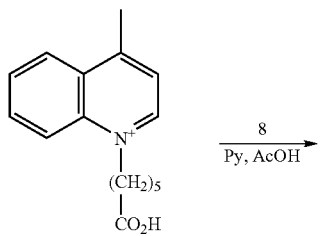

In Scheme 2, trimethylbenz[e]indole is reacted with iodohexanoic acid in acetonitrile to form salt 12, which can then be reacted with compound 8 in pyridine and acetic acid to form fluorescent compound 13. Fluorescent compound 15 can be synthesized from the reaction of compound 8 with lepidium salt 14 generated by reaction of lepidine with iodohexanoic acid in acetonitrile, in pyridine and acetic acid.

Fluorescent compounds 20 and 21 can be synthesized according to the synthesis outlined in Scheme 3.

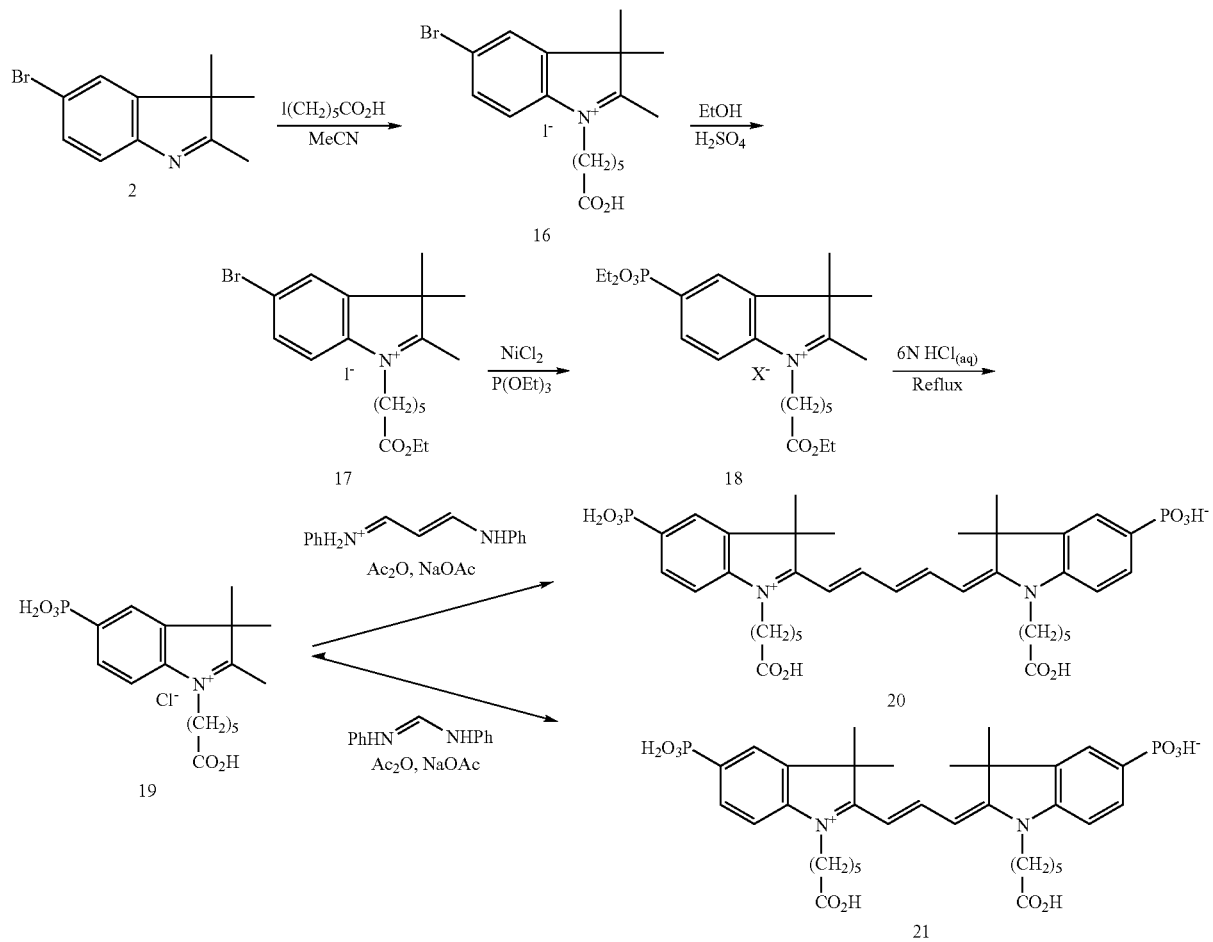

In Scheme 3, compound 2 is reacted with iodohexanoic acid and acetonitrile to produce salt 16, which is esterified by treatment with ethanol and concentrated sulfuric acid to give salt 17. Treatment of salt 17 with triethylphosphite and nickel chloride produces compound 18, which is hydrolyzed to indolium salt 19 with refluxing 6 M hydrochloric acid. Compound 19 can then be reacted with malonaldehyde dianil to form fluorescent compound 20. Alternatively, compound 19 can be reacted with diphenylformamidine to form fluorescent compound 21.

Reacting different combinations of the intermediate compounds can produce new versions of fluorescent compounds. Two examples of this are provided in Scheme 4.

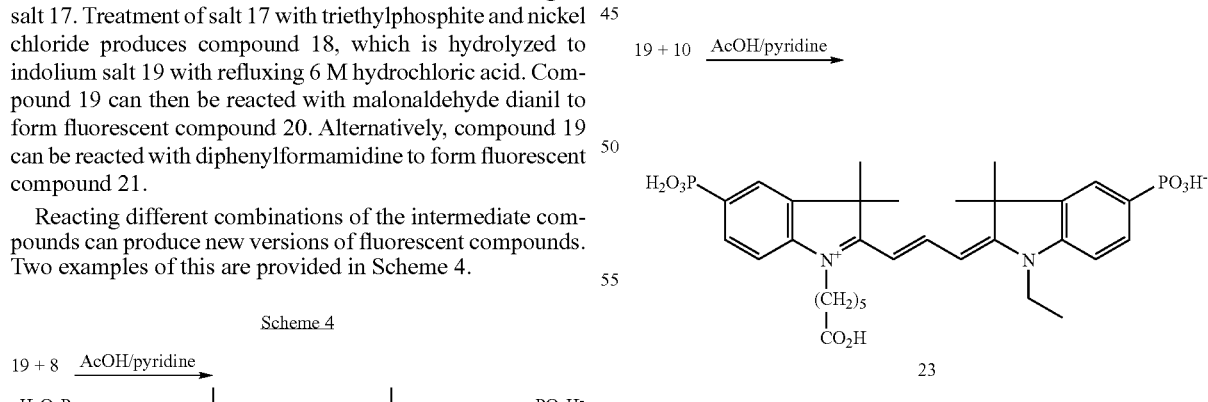

In Scheme 4, compound 19 and compound 8 are reacted with pyridine and acetic acid in order to produce compound 22. Compound 19 can also be reacted with compound 10 in pyridine and acetic acid to form fluorescent compound 23.

Scheme 5 illustrates the formation of some squarane fluorescent compounds.

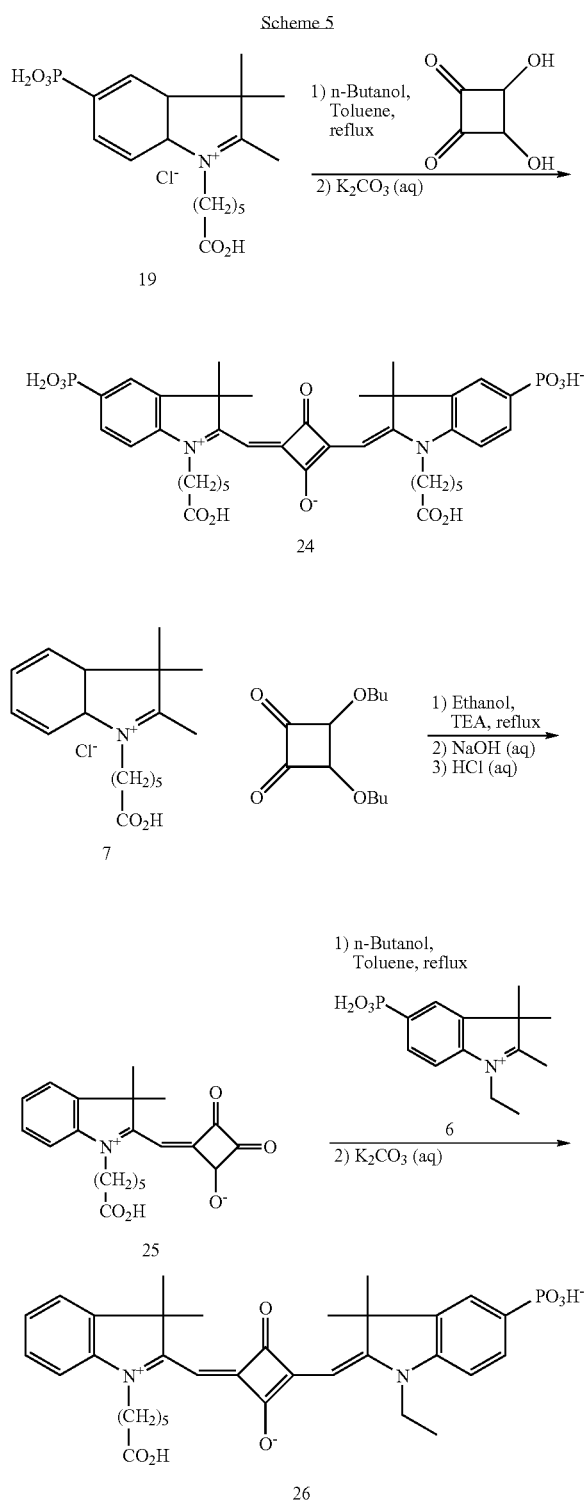

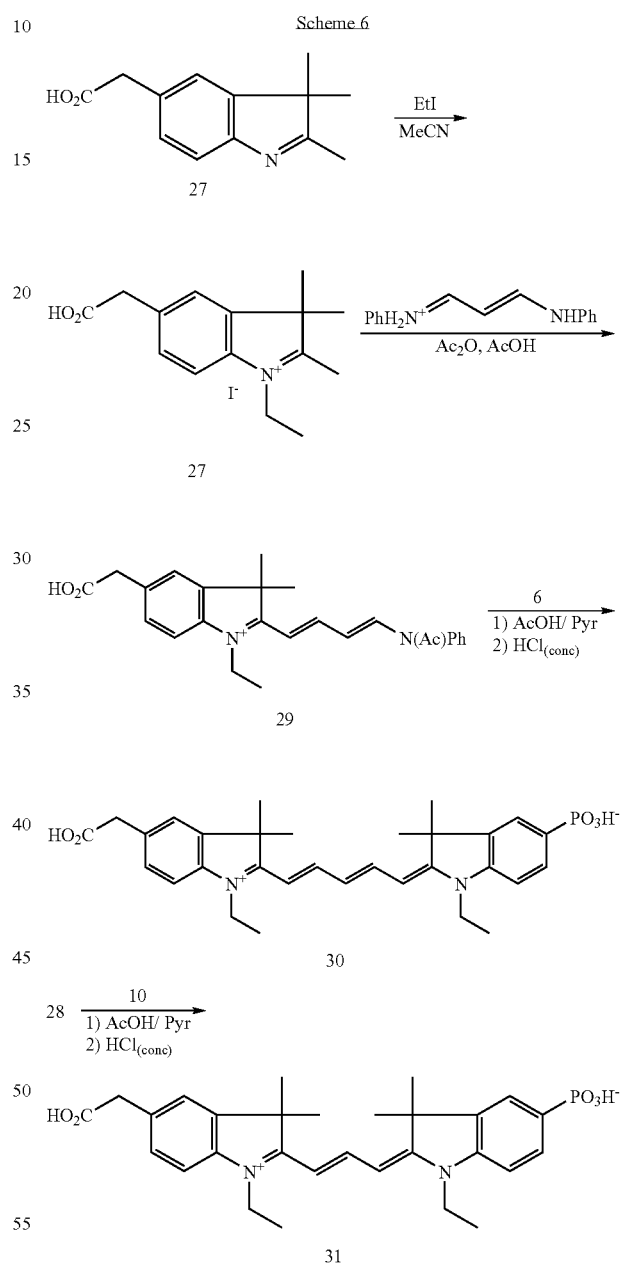

and hydrochloric acid to form compound 25. Compound 25 is then reacted with compound 6 to form fluorescent compound 26.

Fluorescent compounds with carboxylic acid appended to the aromatic residues can be produced according to Scheme 6.

In Scheme 5, compound 19 is reacted with squaric acid in a mixture of n-butanol and toluene. Treatment of the crude reaction products with aqueous potassium carbonate produce fluorescent compound 24. Alternatively, compound 7 can be reacted first with dibutyl squarate and triethylamine in ethanol, and then sequentially with aqueous sodium hydroxide In Scheme 6, compound 27 is reacted with ethyl iodide in acetonitrile to produce compound 28. Compound 28 can be reacted with malonaldehyde dianil to form compound 29 which is reacted with salt 6 to produce fluorescent compound 30. Alternatively, compound 28 can be reacted with compound 10 in order to produce fluorescent compound 31.

Fluorescent compounds with modified cyclohexyl bridging moieties can be produced according to Scheme 7.

Scheme 7

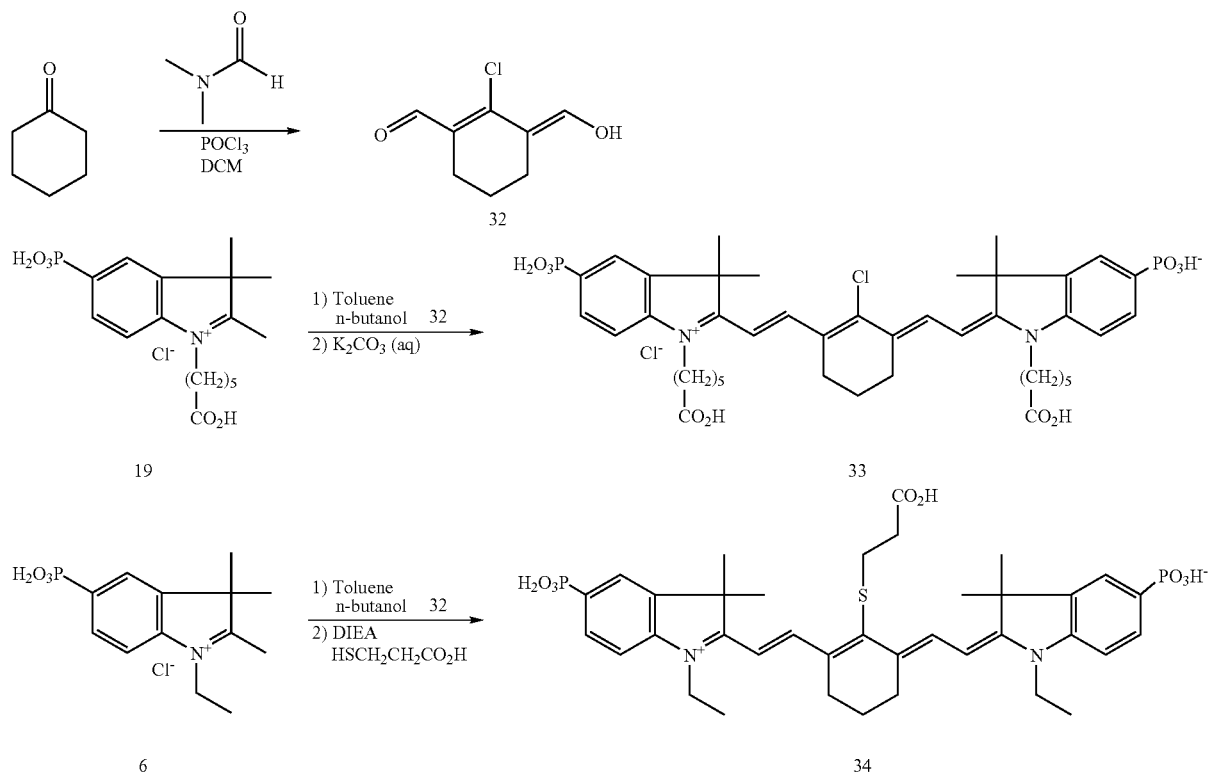

In Scheme 7, cyclohexanone is reacted with N,N dimethylformamide to form compound 32. Compound 19 can then be reacted with compound 32 to produce fluorescent compound 33. Alternatively, compound 6 can be treated sequentially with compound 32 and then with mercaptopropionic acid to produce fluorescent compound 34.

Methods of making the fluorescent compounds of the invention that contain amino groups are outlined in Scheme 8.

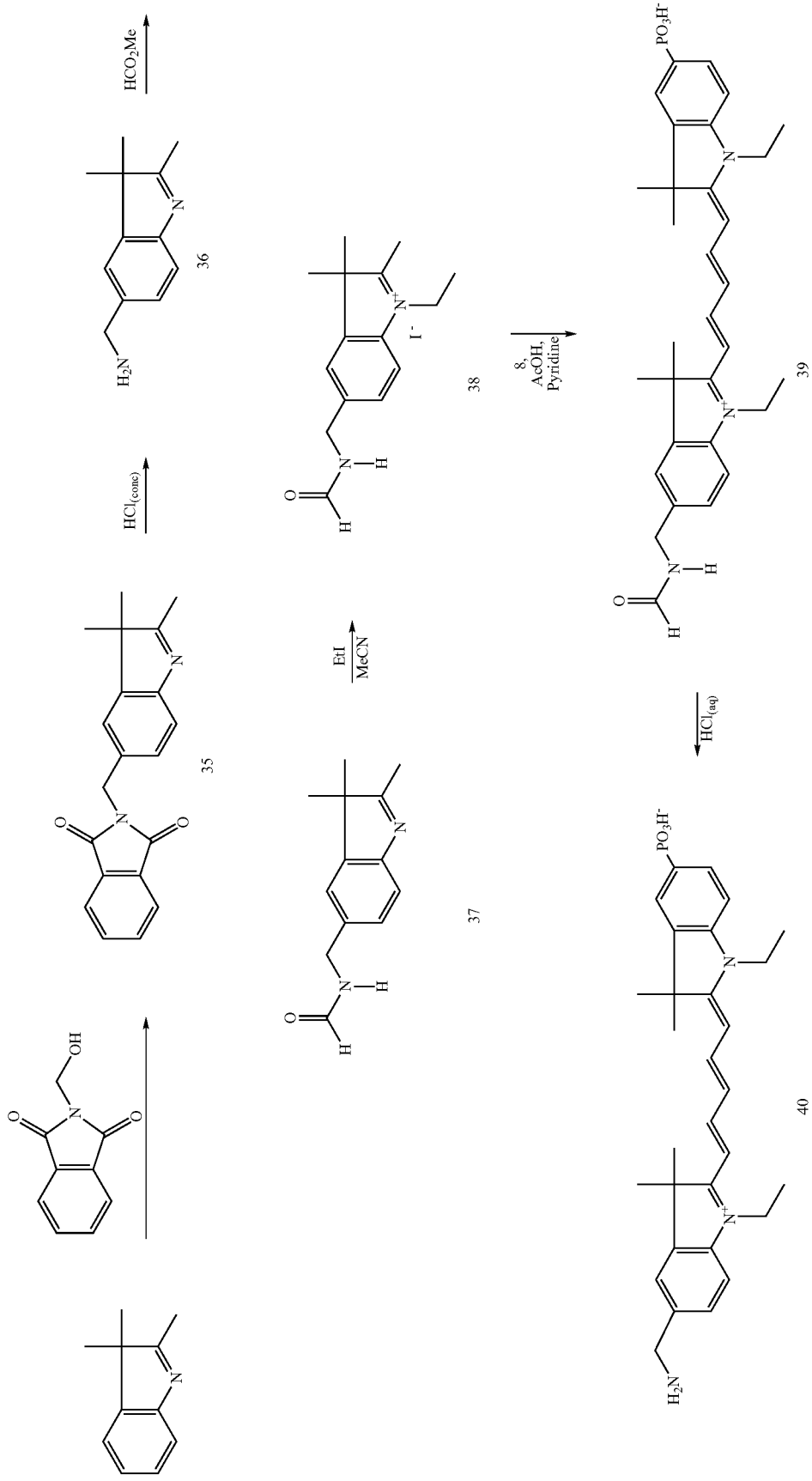

In Scheme 8, hydroxymethylphthalimide is reacted with trimethylindolenine to form compound 35. This group is then hydrolyzed by reaction with conc. HCl to produce compound 36. Compound 36 is then reacted with methyl formate to produce compound 37. Compound 37 is then reacted with ethyl iodide and acetonitrile to produce compound 38. Compound 38 is subsequently reacted with compound 8 is acetic acid and pyridine to produce fluorescent compound 39. Fluorescent compound 39 can then be hydrolyzed to fluorescent compound 40.

Methods of making the fluorescent compounds of the invention that contain additional water solubilizing groups are outlined in Scheme 9.

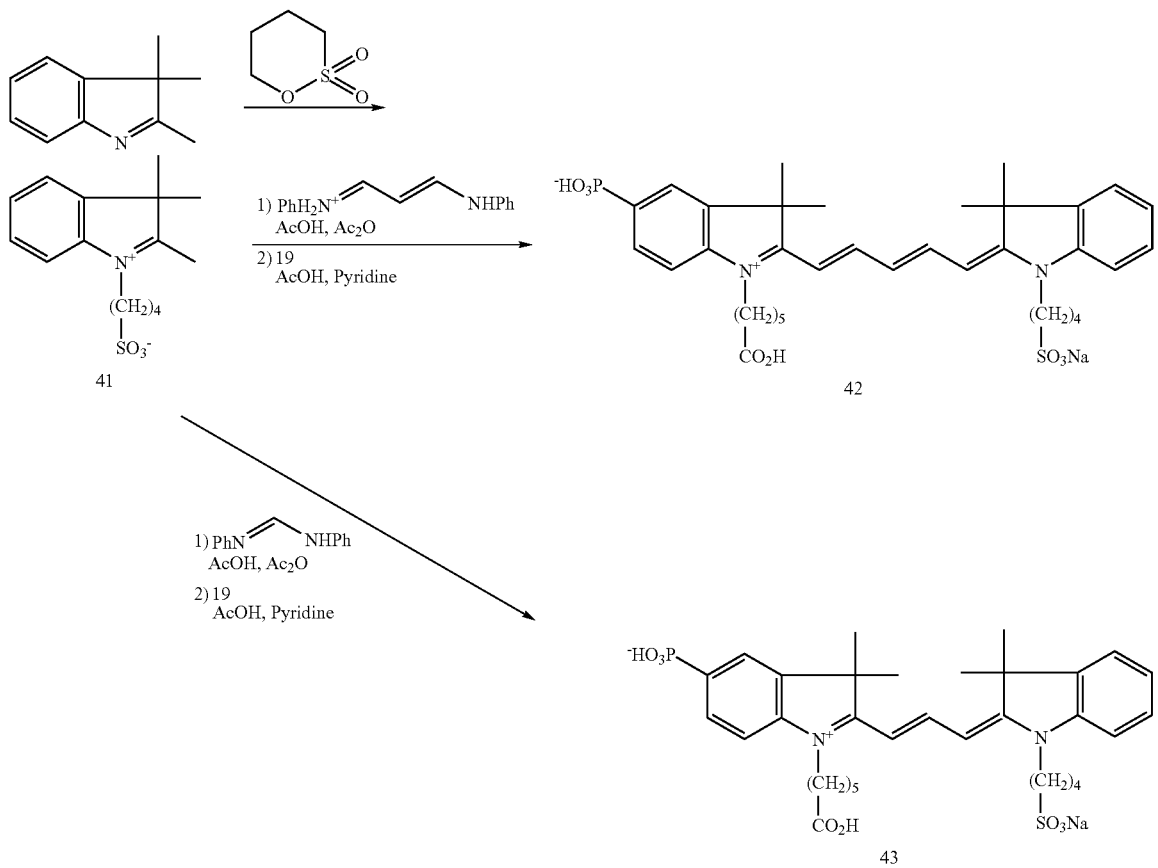

In Scheme 9, trimethylindolenine is reacted with butanesultone to give salt 41. Reaction of 41 with malonaldehyde dianil and then with compound 19 produces fluorescent compound 42. Alternatively, reaction of 41 with diphenylformamidine and then with compound 19 produces fluorescent compound 43.

Several of the fluorescent compounds can be converted into their N-hydroxysuccinimidyl ester analogs according to Scheme 10.

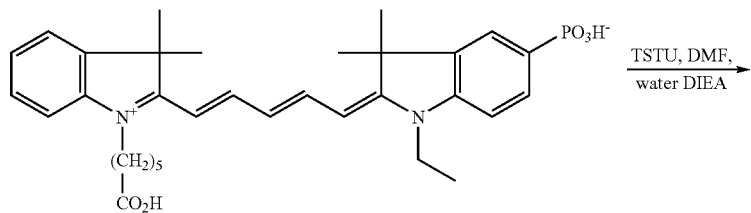

-continued
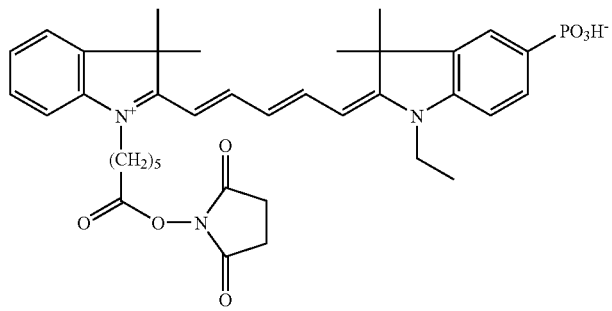
9-OSu
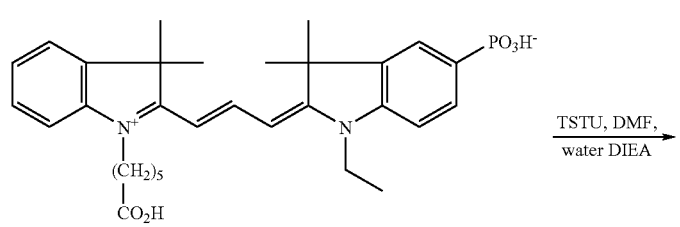
11 → TSTU, DMF, water DIEA
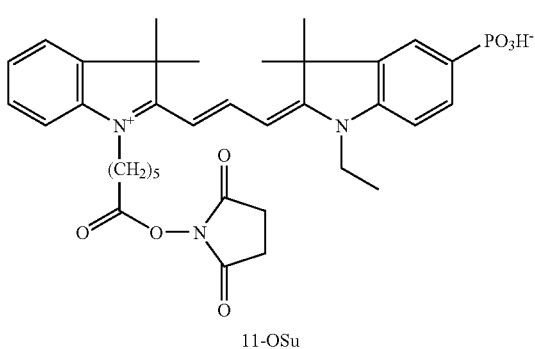
11-OSu
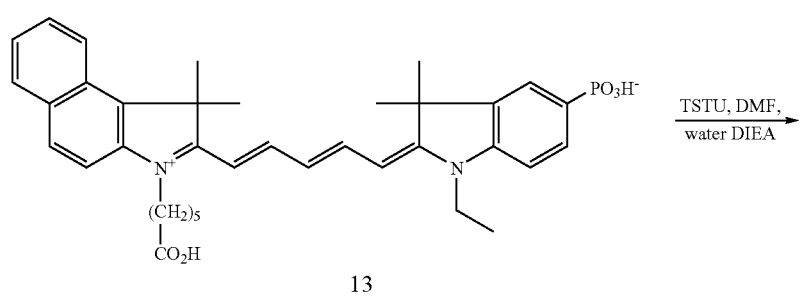
13 → TSTU, DMF, water DIEA
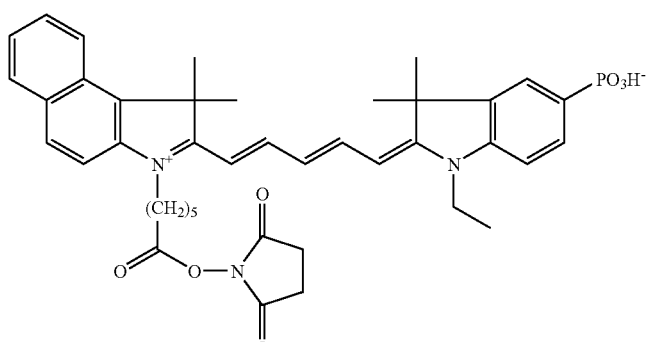
13-OSu

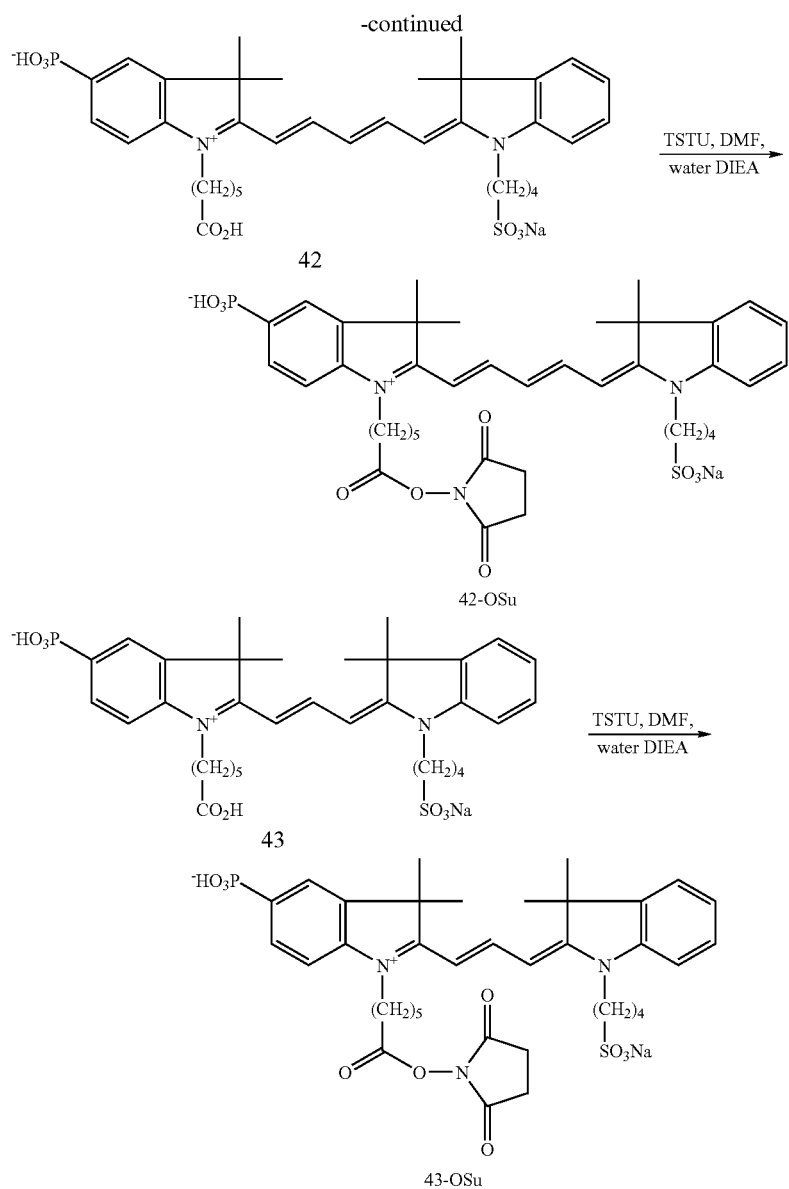

In Scheme 10, compounds 9, 11, 13, 42 and 43 are converted to their respective succinimidyl esters 9-OSu, 11-OSu, 13-OSu, 42-OSu and 43-OSu through reactions with TSTU and DIEA in a mixture of DMF and water.

III. The Methods

Covalent labeling using the fluorescent compounds of the present invention may be utilized either in a biological or a non-biological application. Examples of target molecules that may be labeled in non-biological applications include, for example, cellulose-based materials (including, for example, papers), textiles, petroleum-based products, photographic films, glasses, polymers and gel filtration and chromatography media. These target molecules should have a corresponding functional group as defined in Table 1 which will react with a reactive functional group on the fluorescent compound to form a covalent attachment.

Covalent labeling using fluorescent compounds of the present invention may be accomplished with a target molecule having at least one corresponding reactive functional group as defined hereinbefore. The target molecule may be incubated with an amount of a fluorescent compound of the present invention. $R^1$, $R^2$, $R^3$, $R^{14}$, $R^{15}$, $R^{16}$, $R^{17}$, $R^{18}$, $R^{19}$, $R^{20}$, $R^{21}$, $R^{22}$, $R^{23}$ or $R^{25}$ can be chosen so that the compounds of the present invention react with different target molecules and/or to have different spectral properties, thereby providing a number of related compounds which can be used in multiplex analyses wherein the presence and quantity of various compounds in a single sample must be differentiated based on the wavelengths and intensities of a number of detected fluorescence emissions. The compounds of the present invention may be made soluble in aqueous, other polar, or non-polar media containing the material to be labeled by appropriate selection of R-groups.

Compounds of the present invention may also be used for coupling to additional fluorescent or non-fluorescent compounds for use in fluorescence resonance energy transfer complexes of the type described in EPA 747700 or for fluorescence polarization or fluorescence quenching-based applications.

The present invention is directed to monoclonal antibodies and other components labeled with these fluorescent compounds which are capable of being probes for antigens. When the target molecule is on a type of cell, the present invention can be employed to measure the amount of labeled antibodies which are attached to that type of cell. The measurement can be made by determining the relative brightness or dimness of the luminescence of the cells.

In addition to the foregoing single-step labeling process, the present invention also relates to two-step labeling processes in which, in a first step, a compound of the present invention covalently reacts with and thereby labels a primary component, such as an antibody. In a second or staining step of the two-step procedure, the fluorescently labeled primary component is then used as a probe for a secondary component, such as an antigen for which the antibody is specific. When the partner for the so-labeled antibodies is a cell, the second step of the procedure may be used to determine the amount of labeled antibodies which are attached to that type of cell by determining the intensity of the fluorescence of the cells. By this two-step procedure, monoclonal antibodies and other components covalently labeled in the first step with the fluorescent compounds of the present invention could be used as antigen probes.

The compounds of the present invention can be used to determine the concentration of a particular protein or other component in a system. If the number of reactive groups on a protein which can react with a probe is known, the fluorescence per molecule can be known and the concentration of these molecules in the system can be determined by the total fluorescence intensity of the system. This particular method can be used to measure the concentration of various labeled analytes using microtitre plate readers or other known immunofluorescence detection systems.

The method can be employed to quantify a variety of proteins or other materials in a system by labeling all of a mixture of proteins in the system and then separating the labeled proteins by any means, such as chromatographic means. The amount of separated proteins that are luminescent can then be determined. In chromatographic detection systems, the location of the dye on the labeled material can be ascertained.

This invention can also be employed to determine the number of different cells which are tagged by an antibody. This determination can be made by tagging a plurality of types of cells in a system, and then separating the tagged cells outside of the system. Also, tagged cells can be separated from non-tagged cells outside of the system.

Another embodiment of the present invention comprises a multiparameter method employing a plurality of fluorescent compounds attached respectively to a plurality of different primary components, such as antibodies, each specific for a different secondary component, such as an antigen, in order to identify each of a plurality of said antigens in a mixture of antigens. According to this embodiment, each of said antibodies is separately labeled with a fluorescent compound having a different light absorption and luminescence wavelength characteristics than the dye used for labeling the other probes. Then, the labeled antibodies are all added to a biological preparation being analyzed containing secondary components, such as antigens, which can be respectively stained by particular labeled antibodies. Any unreacted dye materials may be removed from the preparation as by washing, if they interfere with the analysis. The biological preparation is then subjected to a variety of excitation wavelengths, each excitation wavelength used being the excitation wavelength of a particular conjugated fluorescent compound. A luminescence microscope or other luminescence detection system, such as a flow cytometer or fluorescence spectrophotometer, having filters or monochrometers to select the rays of the excitation wavelength and to select the wavelengths of luminescence is employed to determine the intensity of rays of the emission wavelength corresponding to the excitation wavelength. The intensity of luminescence at wavelengths corresponding to the emission wavelength of a particular conjugated fluorescent compound indicates the quantity of antigen which has been bound to the antibody to which the fluorescent compound is attached. In certain cases a single wavelength of excitation can be used to excite luminescence from two or more materials in a mixture where each fluoresces at a different wavelength and the quantity of each labeled species can be measured by detecting its individual fluorescence intensity at its respective fluorescence wavelength. If desired, a light absorption detection method can be employed. The two-step method of the invention can be applied to any system in which a primary material conjugated with a fluorescent compound is used in a luminescence or light absorption detection system to detect the presence of another material to which the primary material-fluorescent compound conjugate is directed. For example, the dye can be conjugated to a fragment of DNA or RNA to form a dye conjugated DNA or RNA fragment which is then directed to a main strand of DNA or RNA to which the piece is complementary. The same test method can be employed to detect the presence of any complementary main strand of DNA.

The fluorescent compounds of this invention are especially well adapted for the analysis of a mixture of components wherein dyes of a variety of excitation and emission wavelengths are required because specific fluorescent compoundscan be synthesized having a wide range of excitation and emission wavelengths. Specific fluorescent compounds having specific excitation and emission wavelengths can be synthesized by varying the number of bridging groups (methine, squarene, etc) or by modifying the ring structures. In this manner, it is possible to synthesize fluorescent compounds having particular excitation wavelengths to correspond to a particular excitation light source, such as a laser, e.g., a HeNe laser or a diode laser.

This invention relates to the covalent reaction of highly luminescent and highly light absorbing fluorescent compounds under reaction conditions to attach amine, hydroxy, aldehyde, sulfhydryl or other groups on proteins, peptides, carbohydrates, nucleic acids, derivatized nucleic acids lipids, certain other biological molecules, biological cells, as well as to non-biological materials, such as soluble polymers, polymeric particles, polymer surfaces, polymer membranes, glass surfaces and other particles and surfaces. Because luminescence involves highly sensitive optical techniques, the presence of these fluorescent compound "labels" can be detected and quantified even when the label is present in very low amounts. Thus, the fluorescent compound reagents can be used to measure the quantity of a material that has been labeled. The most useful dyes are highly light absorbing ($\epsilon$=70,000 to 250,000 liters per mole centimeter, or higher) and very luminescent and they have quantum yields of at least 5% to 80%, or more. The quantities apply to the dyes themselves and to the dyes conjugated to a labeled material.

An important application for these fluorescent compounds is the production of luminescent monoclonal antibodies. Monoclonal antibodies are protein molecules that bind very tightly and very specifically to certain chemical sites or "markers" on cell surfaces or within cells. These antibodies, therefore, have an enormous research and clinical use for identifying certain cell types (e.g., HLA classification, T-cell subsets, bacterial and viral classification, etc.) and diseased cells. In the past, the amount of antibody bound to a cell has been quantified by tagging the antibody in various ways. Tagging has been accomplished with a radioactive label (radio immunoassay), an enzyme (ELISA techniques), or a fluorescent dye (usually fluorescein, rhodamine, TEXAS RED® fluorescent dye or phycoerythrin). Most manufacturers and users of clinical antibody reagents would like to get away from the problems involved in the use of radioactive tracers so luminescence is considered one of the most promising alternatives. In fact, many companies now market fluorescein, TEXAS RED® fluorescent dye, rhodamine and phycoerythrin labeled monoclonal antibodies.

In recent years, optical/electronic instrumentation for detecting fluorescent antibodies on cells has become more sophisticated. For example, flow cytometry can be used to measure the amount of fluorescent antibody on individual cells at a rate up to 5,000 cells per second. Microscopy and solution fluorescence techniques have also advanced. These instruments can excite fluorescence at many wavelengths of the UV, visible, and near IR regions of the spectrum. Yet most of the useful fluorescent labeling reagents available today can be excited only in the 400-580 nm region of the spectrum. The exceptions are some of the phycobiliprotein-type pigments isolated from marine organisms which can be covalently attached to proteins and which can be excited at somewhat longer wavelengths. Therefore, there is a large spectral window ranging from 500 to roughly 900 nm where new labeling reagents need to become available for labeling biological and non-biological materials for analysis with now available instrumentation. New reagents excitable in this spectral region would make it possible to perform multicolor luminescence analyses of markers on cells because antibodies with different specificities could each be tagged with a different colored fluorescent compounds. Thus, the presence of several markers could be determined simultaneously for each cell analyzed.

The fluorescent compounds of the present invention are also useful in assay methodologies that employ fluorescent labels for the detection and measurement of analytes, using for example, fluorescence resonance energy transfer (FRET) based methods, fluorescence lifetime, or by means of fluorescence polarization measurements.

The use of fluorescence resonance energy transfer dye pairs in biological systems is well known and they have been used in the detection of binding events or cleavage reactions in assays which employ FRET. Examples of such assays include equilibrium binding assays, (eg. immunoassays, nucleic acid hybridization assays, protein binding assays and hormone receptor assays) and enzyme assays, such as proteolytic cleavage assays, the cleavage of a DNA or RNA molecule by a nuclease, or a lipid by a lipase.

Binding assays utilizing fluorescent compounds of the present invention may be performed by binding one component of a specific binding pair with a second component of the specific binding pair, the first component being labeled with a fluorescent donor compound according to the present invention, and the second component being labeled with a fluorescent (or quenching) acceptor compound, so as to bring about an energy transfer relationship between the first and second components, and detecting the binding of the first and second components by measurement of the emitted fluorescence. Examples of specific binding pairs include, but are not restricted to, antibodies/antigens,ectins/glycoproteins, biotin/(strept)avidin, hormone/receptor, enzyme/substrate or co-factor, DNA/DNA, DNA/RNA and DNA/binding protein. It is to be understood that in the present invention, any molecule which possess a specific binding affinity for each other may be employed, so that the dyes of the present invention may be used for labeling one component of a specific binding pair, which in turn may be used in the detection of binding to the other component.

The fluorescent compounds of the present invention may also be used in an enzyme cleavage assay format, in which the enzyme substrate, for example a peptide, comprises two components, one of which is labeled with a fluorescent donor compound of the present invention, the second being labeled with a fluorescent (or quenching) acceptor compound and being attached to the substrate in an energy transfer relationship on either side of the substrate bond to be cleaved. A known or a putative enzyme inhibitor compound may be optionally included in the reaction mixture. Cleavage of the substrate by the enzyme results in separation of the donor and acceptor compounds, resulting in a loss of resonance energy transfer and a change in the fluorescence emission of the donor and acceptor species.

Suitable fluorescent acceptor compounds that can be combined with the dyes of the present invention to form energy transfer dye pairs include the rhodamine and cyanine dyes. Particularly preferred are the cyanine dyes, including Cy5 (1-($\epsilon$-carboxypentyl)-1'-ethyl-3,3,3',3'-tetramethyl-5,5'-disulphonato-dicarbocyanine), Cy5,5 (1-($\epsilon$-carboxypentyl)-1'-ethyl-3,3,3',3'-tetramethyl-4,5,4',5'-(1,3-disulphonato)-dibenzo-dicarbocyanine) and Cy7 (1-($\epsilon$-carboxypentyl)-1'-ethyl-3,3,3',3'-tetramethyl-5,5'-disulphon ato-tricarbocyanine). Suitable quenching acceptor dyes are DABCYL (4-(4-dimethylaminophenyl)azobenzoic acid) and Black Hole Quencher dyes.

The fluorescent compounds of the present invention may also be used in binding assays or in enzyme cleavage assays, utilizing fluorescence polarization measurements. In a binding assay format, the assay of an analyte in a sample may be performed by providing a specific binding partner for the analyte, the specific binding partner being labeled with a fluorescent compound according to the present invention, measuring the fluorescence polarization of the labeled specific binding partner, contacting the analyte with the labeled specific binding partner under conditions suitable for binding the analyte to form an analyte-specific binding partner complex and measuring the fluorescence polarization of the labeled analyte-specific binding partner complex to determine the extent of binding.

In the second format, an assay for the detection of enzyme activity may be configured as follows. A reaction mixture is prepared by combining a protease enzyme and a fluorogenic substrate labelled with a fluorescent compound according to the present invention. A known or a putative inhibitor compound may be optionally included in the reaction mixture. Cleavage of the substrate by the enzyme results in the production of labeled fragments. The progress of the reaction is monitored by observing the change in fluorescence polarization.

The fluorescent compound of the present invention can also be used in a detection method wherein a plurality of the fluorescent compounds are covalently attached to a plurality of different primary components, such as antibodies, each primary component being specific for a different secondary component, such as an antigen, in order to identify each of a plurality of secondary components in a mixture of secondary components. According to this method of use, each of the primary components is separately labeled with a fluorescent compound having a different light absorption and emission wavelength characteristic compared with the fluorescent compounds used for labeling the other primary components. The so-called primary components are then added to the preparation containing secondary components, such as antigens, and the primary components are allowed to attach to the respective secondary components for which they are selective.

Any unreacted probe materials may be removed from the preparation by, for example, washing, to prevent interference with the analysis. The preparation is then subjected to a range of excitation wavelengths including the absorption wavelengths of particular fluorescent compounds. A fluorescence microscope or other fluorescence detection system, such as a flow cytometer or fluorescence spectrophotometer, having filters or monochrometers to select the rays of the excitation wavelength and to select the wavelengths of fluorescence is next employed to determine the intensity of the emission wavelengths corresponding to the fluorescent compounds utilized, the intensity of fluorescence indicating the quantity of the secondary component which has been bound with a particular labeled primary component. Known techniques for conducting multi-parameter fluorescence studies include, for example, multi-parameter flow cytometry.

In certain cases a single wavelength of excitation can be used to excite fluorescence from two or more materials in a mixture where each fluoresces at a different wavelength and the quantity of each labeled species can be measured by detecting its individual fluorescence intensity at its respective emission wavelength. If desired, a light absorption method can also be employed.

The detection method of the present invention can be applied to any system in which the creation of a fluorescent primary component is possible. For example, an appropriately reactive fluorescent compound can be conjugated to a DNA or RNA fragment and the resultant conjugate then caused to bind to a complementary target strand of DNA or RNA. Appropriate fluorescence detection equipment can then be employed to detect the presence of bound fluorescent conjugates.

In an exemplary embodiment, the invention provides a method for determining whether a sample contains an enzyme. The method comprises contacting a sample with a peptide construct comprising i) a fluorescent compound according to the invention; ii) a quencher; and iii) a cleavage recognition site for said enzyme, wherein said peptide is in a conformation allowing donor-acceptor energy transfer between the fluorophore and the quencher when the fluorophore is excited. The method also comprises exciting the fluorescent compound. The method also comprises determining a fluorescence property of the sample, wherein the presence of said enzyme in said sample results in a change in said fluorescence property.

In another exemplary embodiment, the invention provides a method for determining whether a compound alters an activity of an enzyme. The method comprises contacting a sample comprising said enzyme and said compound with a peptide construct comprising i) a fluorescent compound according to the invention; ii) a quencher; and iii) a cleavage recognition site for the enzyme, wherein said peptide is in a conformation allowing donor-acceptor energy transfer between the fluorescent compound and the quencher when the fluorescent compound is excited. The method also comprises exciting the fluorescent compound. The method also comprises determining a fluorescence property of the sample, wherein the activity of the enzyme in the sample results in a change in the fluorescence property.

Examples of quencher moieties can be found in the prior art. See, for example, U.S. Pat. Pub. Nos. 20060035262 and 20050272088.

In an exemplary embodiment, the invention provides a method for detecting a nucleic acid target sequence. The method comprises contacting the target sequence with a detector oligonucleotide comprising a target binding sequence, said detector oligonucleotide having linked thereto, i) a fluorescent compound according to the invention; and ii) a quencher, wherein said detector nucleic acid is in a conformation allowing donor-acceptor energy transfer between said fluorescent compound and said quencher when said fluorescent compound is excited. The method also comprises hybridizing said target binding sequence to said single-stranded target sequence, thereby altering said conformation of said detector oligonucleotide, causing a change in a fluorescence parameter. The method also comprises detecting said change in said fluorescence parameter, thereby detecting said nucleic acid target sequence.

In an exemplary embodiment, the complementary strand is synthesized in a target amplification reaction. In another exemplary embodiment, the complementary strand is synthesized by extension of the target sequence using said detector oligonucleotide as a template. In another exemplary embodiment, the fluorescence parameter is detected in real time.

In another aspect, the invention provides a method for detecting amplification of a target sequence comprising, in an amplification reaction, hybridizing to said target sequence a detector oligonucleotide comprising a single-stranded target binding sequence and an intramolecularly associated secondary structure 5' to said target binding sequence, wherein at least a portion of said detector sequence is a single stranded tail which is available for hybridization to said target sequence, said detector oligonucleotide having linked thereto: i) a fluorescent compound according to the invention; and ii) a quencher, wherein said detector nucleic acid is in a conformation allowing donor-acceptor energy transfer between said fluorescent compound and said quencher when said fluorescent compound is excited. The method also comprises extending said hybridized detector oligonucleotide on said target sequence with a polymerase to produce a detector oligonucleotide extension product and separating said detector oligonucleotide extension product from said target sequence. The method also comprises hybridizing a primer to said detector oligonucleotide extension product and extending the primer with said polymerase, thereby linearizing said intramolecularly associated secondary structure and producing a change in a fluorescence parameter. The method also comprises detecting said change in said fluorescence parameter, thereby detecting said target sequence. In an exemplary embodiment, the target sequence is amplified by a method selected from Strand Displacement Amplification, Polymerase Chain reaction, Self Sustained Sequence Replication, Transcription Mediated Amplification, and Nucleic Acid Sequence Based Amplification. In another exemplary embodiment, the secondary structure further comprises a partially or entirely single-stranded restriction endonuclease site. In another exemplary embodiment, a change in fluorescence intensity is detected. In another exemplary embodiment, the change in fluorescence intensity is detected in real-time. In another exemplary embodiment, the intramolecularly associated secondary structure comprises a portion of said target binding sequence.

IV. Assays for Fluorescent Compounds

Protein Labeling Studies

The active esters of the fluorescent compounds 9, 11, 13, 42 and 43 were used to label sheep gamma globulins ("SGG"). The active esters were dissolved in DMSO at a concentration of 0.01 M and quantities of these solutions were added to solutions of SGG in 0.1 M sodium bicarbonate solution (1-2 mg/mL) to provide starting ratios of fluorescent compound to protein of from 1:1 to 60:1. After incubation for a minimum of 18 hours the labeled protein was separated from the hydrolyzed fluorescent compound using a SEPHADEX® G50 gel column with PBS pH 7.3 as an eluant. The labeled proteins were analyzed by absorption and fluorescence spectroscopy.

Oligonucleotide Labeling Studies

The active esters of the fluorescent compounds 9, 11, 13, 42 and 43 were used to label amino modified oligonucleotides. The active esters were dissolved in DMSO at a concentration of 10.0 mg/mL. The CPG with the amino modified oligonucleotide attached was suspended in the active ester solutions. After cleavage of the oligonucleotide from the CPG, the oligonucleotides were isolated by HPLC.

EXAMPLES

General

The following examples are offered to illustrate, but not to limit the claimed invention. In the examples below, unless otherwise stated, temperatures are given in degrees Celsius ° C.; operations were carried out at room or ambient temperature (typically a range of from about 18-25° C.; evaporation of solvent was carried out using a rotary evaporator under reduced pressure (typically, 4.5-400 mm Hg) with a bath temperature of up to 60° C., or by use of a high vacuum oil pump using a room temperature water bath; the course of reactions was typically followed by TLC or RP HPLC and reaction times are provided for illustration only; melting points are uncorrected; products exhibited satisfactory $^1$H-NMR; yields are provided for illustration only; and the following conventional abbreviations are also used: mp (melting point), L (liter(s)), mL (milliliters), mmol (millimoles), g (grams), mg (milligrams), min (minutes), LC-MS (liquid chromatography-mass spectrometry) and h (hours), PS (polystyrene), DIEA (diisopropylethylamine), TSTU (succinimidotetramethyluronium tetrafluoroborate. All reagents and solvents were obtained from Aldrich, Sigma, Kodak, or Fisher, and were used as received unless otherwise stated. NMR spectra were recorded on a 400 MHz spectrometer and were referenced using the residual solvent signal (CD$_3$CN: 1.93, (CD$_3$)$_2$CO: 2.03, CDCl$_3$: 7.26, D$_2$O: 4.65 and D$_6$MSO: 2.50. Absorption spectra were recorded on a HEWLETT PACKARD® HP8453 diode array spectrophotometer and fluorescence spectra were recorded on either a PERKIN ELMER® LS50B or a PHOTON TECHNOLOGY INTERNATIONAL® spectrofluorometer. Quantum yields were determined relative to either rhodamine 6G (Øf=0.95 in ethanol) or Cy5.18 (Øf=0.27 in PBS) as a standard. Flash chromatography refers to the procedure of Still et al [*J. Org. Chem.*, 1978, 43, 2923] and was performed on either silica gel 60 (Merck) or C18 bonded silica gel (Analtech). TLC was performed on either silica gel 60 (Merck) or C18 impregnated silica gel (Analtech) glass plates. DNA fragments were prepared using a BIOSEARCH® 8700 Oligonucleotide Synthesizer.

Example 1

Preparation of 1-(5-carboxy-pentyl)-2-[5-(1-ethyl-3,3-dimethyl-5-phosphono-1,3-dihydro-indol-2-ylidene)-penta-1,3-dienyl]-3,3-dimethyl-3H-indolium (9)

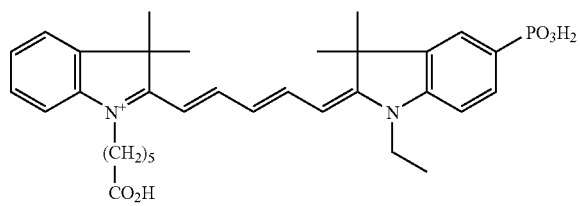

1.1.a Synthesis of p-bromophenylhydrazine (1)

To a 1 L flask were added finely powdered p-bromoaniline (69 g, 0.4 mol), water (200 mL) and conc. HCl (100 mL, 1.2 mol). The mixture was cooled in an ice bath to less than 5° C. A solution of sodium nitrite (30 g, 0.43 mol) in water (90 mL) was added dropwise to the aniline suspension over approx. 1 h, while maintaining the temperature at less than 5° C. The mixture was stirred for a further 30 min and then was gravity filtered through a No. 1 paper into a chilled flask. The solution was added in small portions to a solution of 92% ammonium sulfite (118 g, 0.8 mol) in water (250 mL), which had been chilled to 0° C., at a rate such that the temperature remained at less than 5° C. (approx. 1 h). During the addition a yellow solid formed in the mixture. After the addition was completed, stirring was continued for 1 h at 0° C. and the mixture was then allowed to warm to rt. The solid was filtered off and the filtrate was treated with conc. HCl (120 mL). The solution was heated to reflux during which time a solid formed and then mostly dissolved. The hot solution was filtered and then allowed to cool to rt before chilling in a refrigerator overnight. The crystals were filtered off and were washed with 1 M HCl (60 mL). The solid was added to a mixture of DCM (1 L) and 1N sodium hydroxide (600 mL) and the suspension was shaken until the solid dissolved. The layers were separated and the aqueous phase was washed again with DCM (2×400 mL). The combined organic solutions were dried (MgSO$_4$), filtered and the solvent was evaporated in vacuo to afford p-bromophenylhydrazine (50.3 g, 67%).

1.2.a Synthesis of 5-bromo-2,3,3-trimethyl-3H-indole (2)

To a 500 mL flask were added p-bromophenylhydrazine 1 (50.3 g, 0.27 mol) glacial acetic acid (300 mL) and 3-methylbutanone (40 mL, 0.37 mol). The mixture was heated at reflux for 4 h and then cooled to rt. The volatile components were removed in vacuo and the residue was partitioned between petroleum ether (350 mL) and water (100 mL). The aqueous phase was washed again with petroleum ether (2×100 mL). The combined organic solutions were dried (MgSO$_4$) and filtered and the solvent was evaporated in vacuo to afford 5-bromo-2,3,3-trimethyl-3H-indole 2 (56.3 g, 87%).

1.2.b Characterization of 5-bromo-2,3,3-trimethyl-3H-indole (2)

$^1$H NMR (CDCl$_3$) 1.27 (s, 6H), 2.23 (s, 3H) and 7.35-7.43 (m, 3H). $^{13}$C NMR (CDCl$_3$) 15.5, 23.0, 54.2, 118.9, 121.4, 124.9, 130.7, 147.9, 152.7, 188.5.

1.3.a Synthesis of 5-bromo-1-ethyl-2,3,3-trimethyl-3H-indolium iodide (3)

To a 250 mL flask were added bromotrimethylindole 2 (12 g, 50.4 mmol), acetonitrile (25 mL) and ethyl iodide (20 mL). The mixture was heated at reflux under argon for 40 h. The bulk of the volatile components were removed by distillation. The residue was triturated with ether (100 mL) to give a powder. The solid was filtered off, washed with ether (2×50 mL) and dried under high vacuum to afford 3 as a solid (17.3 g, 87%).

1.3.b Characterization of 5-bromo-1-ethyl-2,3,3-trimethyl-3H-indolium iodide (3)

$^1$H NMR (D$_6$-DMSO) 1.42 (t, J=7.3 Hz, 3H), 1.55 (s, 6H), 2.84 (s, 3H), 4.48 (quartet, J=7.3 Hz, 2H), 7.78 (dd, J=1.9 Hz and J=8.6 Hz, 1H), 7.96 (d, J=8.6 Hz, 1H) and 8.19 (d, J=1.9 Hz, 1H). $^{13}$C NMR 13.2, 14.7, 22.3, 43.9, 55.0, 117.9, 123.3, 127.5, 132.4, 140.6, 144.8, 197.2.

1.4.a Synthesis of (1-ethyl-3,3-dimethyl-2-methylene-2,3-dihydro-1H-indol-5-yl)-phosphonic acid diethyl ester (5)

To a 250 mL flask were added 3 (9.6 g, 20 mmol) and nickel chloride (0.52 g, 4.0 mmol). The flask was fitted with a dropping funnel and a condenser and was then lowered into an oil bath. The mixture was heated to 175° C. At approx. 165° C. triethylphosphite (15 mL, 86 mmol) was added dropwise. The mixture fizzed and became dark before turning to a dark straw color. After heating at 175° C. for 30 min a second portion of nickel chloride (0.52 g, 4.0 mmol) was added. The mixture fizzed vigorously, gave off much vapor and became dark grey-green in color. Heating was continued for 30 min and then the reaction was cooled to rt. The mixture was treated with methanol (100 mL) and filtered through a bed of celite. The methanol was evaporated in vacuo to leave an oil that was fractionally distilled on a KUGELROHR® vacuum distillation apparatus to afford 5 as a colorless liquid (4.0 g, 62%). The oil was stored under argon.

1.5.a Synthesis of 1-ethyl-2,3,3-trimethyl-5-phosphono-3H-indolium (6)

To a 250 mL flask were added 5 (4.0 g, 12.3 mmol) and 6 M HCl (60 mL). The mixture was stirred at rt until the oil dissolved and was then heated at reflux overnight. After cooling, the mixture was filtered and was evaporated to dryness in vacuo. The residue was treated with water (100 mL) and, after stirring for 30 min, was filtered. The aqueous solution was washed with DCM (2×60 mL), filtered and concentrated in vacuo to approx 4-6 mL. The solution was loaded onto a column of C18-reversed phase silica gel (7×15 cm) in water. The column was eluted with water. Pure fractions (by RP HPLC) were collected and the solvent evaporated in vacuo to afford 6 as an off-white solid that was dried over phosphorous pentoxide and then stored under argon.

1.5.b Characterization of 1-ethyl-2,3,3-trimethyl-5-phosphono-3H-indolium (6)

$^1$H NMR (D$_2$O) 1.42 (t, J=7.4 Hz, 3H), 1.45 (s, 6H), 4.38 (quartet, J=7.4 Hz, 2H), 7.70 (dd, J=8.3 Hz and 1.7 Hz, 1H), 7.78-7.84 (m, 1H) and 7.88 (d, J=12.1 Hz). $^{13}$C NMR 12.1, 21.4, 43.5, 54.6, 115.1, 125.2, 131.4, 134.6, 136.4, 141.9, 142.7, 197.7.

1.6.a Synthesis of 1-(5-carboxypentyl)-2,3,3'-trimethyl-3H-indolium iodide (7)

To a 250 mL flask were added trimethylindolenine (73.5 g, 462 mmol), acetonitrile (300 mL) and 6-iodohexanoic acid (117.3 g, 485 mmol). The mixture was heated at reflux under argon for 40 h. Approximately 150 mL of the acetonitrile was removed by distillation and then the mixture was poured slowly into stirred ethyl acetate (1.5 L). Stirring was continued for 1 hour and then the solid was filtered off and was washed with ethyl acetate (2×200 mL). The solid was dried under high vacuum to afford 7 as a tan colored solid (69.8 g, 58%).

1.7.a Synthesis of Fluorescent Compound 9

To a 50 mL flask were added compound 6 (0.48 g, 1.79 mmol), malonaldehyde dianilide hydrochloride (0.518 g, 2.0 mmol), acetic acid (5 mL) and acetic anhydride (5 mL). The mixture was heated at 110° C. for 3 h and was then cooled to rt. The volatile components were removed under vacuum to leave a tar containing 8. The tar was washed with ether (2×60 mL) and then dissolved in acetic acid (5 mL). To the mixture were added 7 (0.65 g, 1.83 mmol) and pyridine (6 mL). The mixture was heated at 110° C. for 1 h and then cooled to rt. The volatile components were removed in vacuo and the residue was dissolved in conc. HCl (30 mL). After stirring for 3 h, the mixture was diluted with water (200 mL) and then basified by addition of saturated sodium bicarbonate solution. The fluorescent compound initially precipitated from the mixture but then re-dissolved. The aqueous solution was loaded onto a column of C-18 reverse-phase silica gel (4×15 cm) in water. The column was eluted with water to remove the inorganic salts and excess base, with 1 M HCl to generate the free acid of the fluorescent compound and then with water to remove the excess acid. Gradient elution from 0-50% methanol in water (5% steps of 500 mL-1 L) first eluted the symmetrical bisphosphonic acid fluorescent compound and then fluorescent compound 9. Those fractions containing 9 were combined and the solvent was evaporated in vacuo to leave a blue residue that was taken up in methanol and filtered through a medium frit. The methanol was removed in vacuo and the residue was washed with acetonitrile. The solid was dried under vacuum to give fluorescent compound 9 as a blue solid (0.456 g, 44%).

1.7.b Characterization of Fluorescent Compound 9

$^1$H NMR (CD$_3$OD) 1.37 (t, J=7.4 Hz, 3H), 1.46-1.55 (m, 2H), 1.64-1.75 (m, 14H), 1.84 (quintet, J=7.4 Hz, 2H), 2.32 (t, J=7.3 Hz, 2H), 4.11-4.17 (m, 4H), 6.26-6.34 (m, 2H), 6.64 (t, J=12.4 Hz, 1H), 7.25-7.33 (m, 3H), 7.39-7.44 (m, 1H), 7.50 (d, J=7.2, 1H), 7.84-7.90 (m, 2H) and 8.22-8.31 (m, 2H). $^{13}$C NMR 11.2, 24.4, 26.0, 26.6, 26.9, 33.4, 38.6, 43.5, 49.0, 49.4, 102.7, 103.4, 109.4, 109.6, 110.9, 122.1, 124.6, 124.7, 125.5, 128.5, 131.4, 131.5, 133.5, 135.3, 140.5, 140.6, 141.5, 142.1, 142.9, 172.8, 173.8, 176.0.

Example 2

Preparation of 1-(5-carboxy-pentyl)-2-[3-(1-ethyl-3,3-dimethyl-5-phosphono-1,3-dihydro-indol-2-ylidene)-propenyl]-3,3-dimethyl-3H-indolium (11)

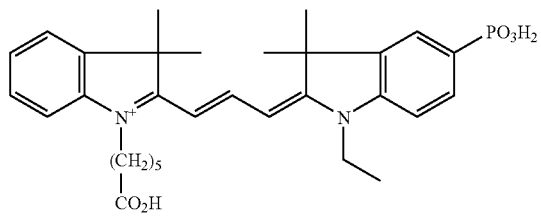

2.1.a Synthesis of Fluorescent Compound 11

To a 50 mL flask were added 6 (0.31 g, 1.16 mmol), diphenylformamidine (0.30 g, 1.53 mmol), acetic acid (2 mL)

and acetic anhydride (2 mL). The mixture was heated at 120° C. for 90 min and then was cooled to rt. The volatile components were removed under vacuum to leave a tar that was then washed with ether (2×30 mL) to afford 10. The tar was dissolved in acetic acid (2 mL) and then pyridine (4 mL) and 7 (0.40 g, 1.14 mmol) were added. The mixture was heated at 120° C. for 45 min and then cooled to rt. The volatile components were removed in vacuo and the residue was dissolved in conc. HCl. After stirring for 3 h the mixture was diluted with water (200 mL) and then basified by addition of saturated sodium bicarbonate solution. Fluorescent compound initially precipitated from the mixture but then re-dissolved. The aqueous solution was loaded onto a column of C-18 reverse-phase silica gel (4×15 cm) in water. The column was eluted with water to remove the salts and excess base, with 1 M HCl to generate the free acid of the fluorescent compound and then with water to remove the excess acid. Gradient elution from 0-50% methanol in water (5% steps of 500 mL-1 L) first eluted the symmetrical bisphosphonic acid fluorescent compound and then fluorescent compound 11. The fractions were evaporated in vacuo to leave a red residue that was taken up in methanol and filtered through a medium frit. The methanol was removed in vacuo and the residue was washed with acetonitrile. The solid was dried under vacuum to give fluorescent compound 11 as a red solid (0.32 g, 51%).

2.1.b Characterization of Fluorescent Compound 11

$^1$H NMR (CD$_3$OD) 1.40 (t, J=7.3 Hz, 3H), 1.51-1.58 (m, 2H), 1.67-1.78 (m, 14H), 1.88 (quintet, J=7.4 Hz, 2H), 2.33 (t, J=7.4 Hz, 2H), 4.18-4.24 (m, 4H), 6.48-6.56 (m, 2H), 7.32-7.50 (m, 4H), 7.58 (d, J=7.0 Hz, 1H), 7.86-7.93 (m, 2H) and 8.57 (t, J=13.4 Hz, 1H). $^{13}$C NMR 11.2, 24.4, 26.0, 26.9, 27.0, 33.3, 39.0, 44.0, 49.1, 49.6, 102.2, 103.3, 110.1, 110.3, 111.5, 122.3, 124.6, 124.7, 125.6, 128.8, 130.5, 131.8, 131.9, 132.3, 140.4, 140.5, 141.1, 143.7, 151.2, 174.1, 175.5, 175.9.

Example 3

Preparation of 3-(5-carboxy-pentyl)-2-[5-(1-ethyl-3,3-dimethyl-5-phosphono-1,3-dihydro-indol-2-ylidene)-penta-1,3-dienyl]-1,1-dimethyl-1H-benzo[e]indolium (13)

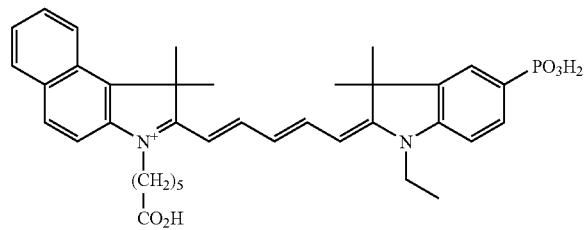

3.1.a Synthesis of 3-(5-carboxy-pentyl)-1,1,2-trimethyl-1H-benzo[e]indolium iodide (12)

To a 250 mL flask were added trimethylbenz[e]indole (5.21 g, 24.9 mmol), acetonitrile (80 mL) and 6-iodohexanoic acid (6.5 g, 26.9 mmol). The mixture was heated at reflux under argon for 1 h and then approx. 70 mL of the acetonitrile was removed by distillation. The mixture was heated at 100° C. for 20 h. The green mixture of solid and liquid was cooled to rt and the volatile components were removed in vacuo. The residue was triturated with ether (2×60 mL), ethyl acetate (2×60 mL) and with ether (2×60 mL) to give 12 as a powder (8.51 g, 75%).

3.1.b Characterization of 3-(5-carboxy-pentyl)-1,1,2-trimethyl-1H-benzo[e]indolium iodide (12)

$^1$H NMR (D$_6$-DMSO) 1.43-1.48 (m, 2H), 1.58 (quintet, J=7.5 Hz, 2H), 1.76 (s, 6H), 1.90 (quintet, J=7.2 Hz, 2H), 2.23 (t, J=7Hz, 2H), 2.94 (s, 3H), 4.58 (t, J=7.5 Hz, 2H), 7.71-7.78 (m, 2H) 8.15 (d, J=9.0 Hz, 1H), 8.22 (d, J=8.7 Hz, 1H), 8.29 (d, J=8.7 Hz, 1H) and 8.37 (d, J=7.7 Hz, 1H).

3.2.a Synthesis of 3-(5-carboxy-pentyl)-2-[5-(1-ethyl-3,3-dimethyl-5-phosphono-1,3-dihydro-indol-2-ylidene)-penta-1,3-dienyl]-1,1-dimethyl-1H-benzo[e]indolium (13)

To a 50 mL flask were added 6 (0.45 g, 1.68 mmol), malonaldehyde dianilide hydrochloride (0.45 g, 1.74 mmol), acetic acid (4 mL) and acetic anhydride (4 mL). The mixture was heated at 110° C. for 90 min and then was cooled to rt. The volatile components were removed under vacuum to leave a tar. The tar was dissolved in acetic acid (4 mL) and then pyridine (5 mL) and 12 (0.74 g, 1.64 mmol) were added. The mixture was heated at 110° C. for 25 min and then cooled to rt. The volatile components were removed under vacuum to leave a dark blue tar that was dissolved in conc. HCl (30 mL). After stirring for 3 h the mixture was diluted with water (200 mL) and then basified, first by addition of 4 M sodium hydroxide solution until the pH was approx. 4 and then with saturated sodium bicarbonate solution. Fluorescent compound initially precipitated from the mixture but then re-dissolved. The aqueous solution was loaded onto a column of C-18 reverse-phase silica gel (4×15 cm) in water. The column was eluted with water to remove the salts and excess base, with 1 M HCl to generate the free acid of the fluorescent compound and then with water to remove the excess acid. Gradient elution from 0-55% methanol in water (5% steps of 500 mL-1 L) first eluted the symmetrical bisphosphonic acid fluorescent compound and then fluorescent compound 13. The fractions were evaporated in vacuo to leave a blue residue that was taken up in methanol (70 mL) and filtered through a medium frit. Water (30 mL) was added and then the solvent mixture was removed in vacuo to afford fluorescent compound 13 as a blue solid (0.57 g, 55%).

3.2.b Characterization of Fluorescent Compound 13

$^1$H NMR (CD$_3$OD) 1.38 (t, J=7.2 Hz, 3H), 1.52-1.58 (m, 2H), 1.67-1.74 (m, 8H), 1.87-1.98 (m, 2H), 2.02 (s, 6H), 2.32 (t, J=7.3 Hz, 2H), 4.13 (quartet, J=7.1 Hz, 2H), 4.26 (t, J=7.4 Hz, 2H), 6.27 (d, J=13.7 Hz, 1H), 6.38 (d, J=13.9 Hz, 1H), 6.65 (t, J=12.4 Hz, 1H), 7.22-7.26 (m, 1H), 7.48-7.52 (m, 1H), 7.60-7.68 (m, 2H), 7.83-7.89 (m, 2H), 7.99-8.04 (m, 2H) and 8.37 (t, J=13.1 Hz, 1H).

Example 4

Preparation of 1-(5-carboxy-pentyl)-4-[5-(1-ethyl-3,3-dimethyl-5-phosphono-1,3-dihydro-indol-2-ylidene)-penta-1,3-dienyl]-quinolinium chloride (15)

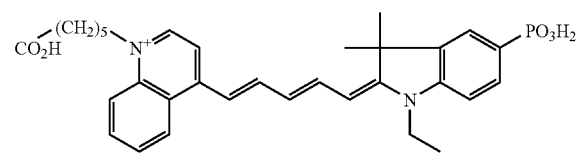

4.1.a Synthesis of 1-(5-carboxy-pentyl)-4-methyl-quinolinium iodide (14)

To a 250 mL flask were added lepidine (7.5 g, 52.4 mmol), acetonitrile (40 mL) and 6-iodohexanoic acid (14.0 g, 57.9 mmol). The mixture was heated at reflux under argon for 40 h and then was cooled to rt. The mixture was poured into stirred ether (700 mL) and the stirring was continued until the supernatant liquid was clear. The supernatant was decanted and the residue was dissolved in DCM (60 mL). The solution was poured slowly into stirred ether (700 mL). The initially formed oil solidified after stirring for approx. 3 h. The solid was crushed to a powder and stirring was continued for 1 h. The solid was filtered off, washed with ether (2×60 mL), and dried under vacuum to afford 14 as a tan colored solid (17.6 g, 87%).

4.1.b Characterization of 1-(5-carboxy-pentyl)-4-methyl-quinolinium iodide (14)

$^1$H NMR (D$_6$-DMSO) 1.34-1.43 (m, 2H), 1.58 (quintet, J=7.7 Hz, 2H), 1.95 (quintet, J=7.5Hz, 2H), 2.21 (t, J=7.3 Hz, 2H), 3.01 (s, 3H), 5.00 (t, J=7.5 Hz, 2H), 8.03-8.08 (m, 2H), 8.23-8.28 (m, 1H), 8.53-8.56 (m, 1H), 8.59 (d, J=9.0 Hz, 1H), 9.41 (d, J=6.0 Hz, 1H)

4.2.a Synthesis of 1-(5-carboxy-pentyl)-4-[5-(1-ethyl-3,3-dimethyl-5-phosphono-1,3-dihydro-indol-2-ylidene)-penta-1,3-dienyl]-quinolinium chloride (15)

To a 50 mL flask were added 6 (0.25 g, 0.93 mmol), malonaldehyde dianilide hydrochloride (0.25 g, 0.97 mmol), acetic acid (4 mL) and acetic anhydride (4 mL). The mixture was heated at 110° C. for 90 min and then was cooled to rt. The volatile components were removed under vacuum to leave a tar. The tar was dissolved in acetic acid (4 mL) and then pyridine (5 mL) and 14 (0.34 g, 0.89 mmol) were added. The mixture was heated at 110° C. for 25 min and then cooled to rt. The volatile components were removed under vacuum to leave a dark blue tar that was dissolved in conc. HCl (20 mL). After stirring for 3 h, the mixture was diluted with water (150 mL) and then basified, first by addition of 4 M sodium hydroxide solution until the pH was approx. 4 and then with saturated sodium bicarbonate solution. The fluorescent product initially precipitated from the mixture but then re-dissolved. The aqueous solution was loaded onto a column of C-18 reverse-phase silica gel (4×15 cm) in water. The column was eluted with water to remove the salts and excess base, with 1 M HCl to generate the free acid of the fluorescent compound and then with water to remove the excess acid. Gradient elution from 0-55% methanol in water (5% steps of 500 mL-1 L) first eluted the symmetrical bisphosphonic acid fluorescent compound and then fluorescent compound 15. The fractions were evaporated in vacuo to leave a blue residue that was taken up in methanol (70 mL) and filtered through a medium frit. Water (30 mL) was added and then the solvent mixture was removed in vacuo to afford fluorescent compound 15 as a blue solid.

4.2.b Characterization of Fluorescent Compound 15

$^1$H NMR (CD$_3$OD) 1.30 (t, J=6.8 Hz, 3H), 1.46-1.53 (m, 2H), 1.62-1.71 (m, 8H), 2.00-2.04 (m 2H), 2.31 (t, J=7.2 Hz, 2H), 3.89-3.93 (m, 2H), 4.73 (t, J=7.4 Hz, 2H), 5.90 (d, J=11.8 Hz, 1H), 6.59-6.65 (m, 1H), 6.97 (dd, J=2.5 Hz and J=8.4 Hz, 1H), 7.29 (t, J=14Hz, 1H), 7.67-7.85 (m, 4H), 7.96 (d, J=6.9 Hz, 1H), 8.03-8.23 (m, 3H) and 8.59-8.64 (m, 2H)

Example 5

Preparation of 1-(5-carboxy-pentyl)-2-[5-(1-(5-carboxy-pentyl)-3,3-dimethyl-5-phosphono-1,3-dihydro-indol-2-ylidene)-penta-1,3-dienyl]-3,3-dimethyl-5-phosphono-3H-indolium (20)

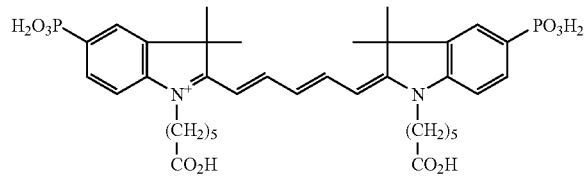

5.1.a Synthesis of 5-bromo-1-(5-carboxy-pentyl)-2,3,3-trimethyl-3H-indolium iodide (16)

To a 250 mL flask were added bromotrimethylindolenine (5.8 g, 24 mmol), acetonitrile (25 mL) and 6-iodohexanoic acid (5.1 g, 21 mmol). The mixture was heated at reflux under argon for 40 h and then the bulk of the volatile components were removed by distillation and then the mixture was heated at 140° C. for 2 h. The mixture was cooled and was triturated with DCM (100 mL) to give a powder. The solid was filtered off, was washed with DCM (2×50 mL) and was dried under high vacuum to afford 16 (8.7 g, 87%).

5.1.b Characterization of 5-bromo-1-(5-carboxy-pentyl)-2,3,3-trimethyl-3H-indolium iodide (16)

$^1$H NMR (D$_6$-DMSO) 1.43-1.48 (m, 2H), 1.50-1.55 (m, 8H), 1.82 (quintet, J=7.5 Hz, 2H), 2.22 (t, J=7.1 Hz, 2H), 2.83 (s, 3H), 4.44 (t, J=7.6 Hz, 2H), 7.82-7.85 (m, 1H), 7.95 (d, J=8.5 Hz, 1H) and 8.19 (d, J=1.7 Hz, 1H). $^{13}$C NMR 14.7, 22.4, 24.6, 25.9, 27.433.9, 48.2, 55.0, 118.0, 123.4, 127.5, 132.4, 140.9, 144.7, 174.9, 197.6.

5.2.a Synthesis of 5-bromo-1-(5-ethoxycarbonyl-pentyl)-2,3,3-trimethyl-3H-indolium iodide (17)

To a 250 mL flask were added 16 (2.0 g, 4.17 mmol), ethanol (60 mL) and conc. sulfuric acid (0.2 mL). The mixture was heated at reflux for 2 h and then was cooled to rt. The ethanol was removed in vacuo and the residue was partitioned between water (40 mL) and DCM (80 mL). The organic layer was washed with 1 M HCl (40 mL), water (40 mL) and then with a solution of sodium iodide. It was dried (MgSO$_4$) and evaporated in vacuo to afford 17 as a brown solid (1.74 g, 82%).

5.2.b Characterization of 5-bromo-1-(5-ethoxycarbonyl-pentyl)-2,3,3-trimethyl-3H-indolium iodide (17)

$^1$HNMR (D$_6$-DMSO) 1.15 (t, J=7.1 Hz, 3H), 1.43-1.48 (m, 2H), 1.53-1.60 (m, 8H), 1.82 (quintet, J=7.5 Hz, 2H), 2.29 (t, J=7.3 Hz, 2H), 2.84 (s, 3H), 4.02 (quarter, J=7.1 Hz, 2H), 4.44 (t, J=7.5 Hz, 2H), 7.83-7.86 (m, 1H), 7.95 (d, J=8.6 Hz, 1H) and 8.19 (d, J=1.7 Hz, 1H). $^{13}$C NMR 14.7, 14.8, 22.4, 24.6, 25.8, 27.4, 33.7, 48.2, 55.0, 60.3, 118.0, 123.4, 127.5, 132.4, 141.0, 144.7, 173.3, 197.6.

5.3.a Synthesis of (1-(5-ethoxycarbonyl-pentyl)-3,3-dimethyl-2-methylene-2,3-dihydro-1H-indol-5-yl)-phosphonic acid diethyl ester (18)

To a 3-neck 500 mL flask were added 5-bromo-1-(5-carboxy-pentyl)-2,3,3'-trimethylindoline (8.4 g, 22.1 mmol) and nickel chloride (0.72 g, 5.6 mmol). The flask was fitted with a dropping funnel and the system was flushed with argon. The mixture was heated to 170° C. and then triethyl phosphite (30 mL, 173 mmol) was added dropwise over 30 min. The temperature was raised to 180° C. and then nickel chloride (0.72 g, 5.6 mmol) was added. After about 10 seconds rapid fizzing occurred and the mixture turned grey-green in color. After heating for a further 30 min the mixture was cooled to rt and treated with DCM (200 mL). The mixture was filtered through a fiber glass filter pad and then the DCM was removed in vacuo. The excess triethyl phosphite and volatile components were removed using a KUGELROHR® vacuum distillation apparatus (110° C. @ 0.4 mm Hg). The residue was subjected to column chromatography on silica gel (6×14 cm) using 2.5-10% methanol in DCM as an eluant. Fractions containing the product had a tendency to turn pink upon exposure to air. Evaporation of the fractions afforded 18 as a pink oil (8.0 g, 86%). The oil was stored under argon.

5.4.a Synthesis of 1-(5-carboxy-pentyl)-2,3,3-trimethyl-5-phosphono-3H-indolium (19)

To a 500 mL round bottom flask were added 18 (8.0 g, 18.3 mmol) and 6 M HCl (280 mL). The mixture was stirred at rt until the oil dissolved and was then heated at refluxf overnight. After cooling, the mixture was filtered and evaporated to dryness in vacuo. The residue was treated with water (100 mL) and, after stirring for 20 min, was filtered. The aqueous solution was concentrated in vacuo to approx. 10 mL and then was loaded onto a column of reversed phase silica gel (6×18 cm) in water. The column was eluted with water. Fractions were analyzed by RP HPLC. Evaporation of the fractions in vacuo afforded 19 as an off-white solid that was dried over phosphorous pentoxide and then stored under argon (5.3 g, 76%).

5.4.b Characterization of 1-(5-carboxy-pentyl)-2,3,3-trimethyl-5-phosphono-3H-indolium (19)

$^1$H NMR (D$_2$O) 1.26-1.34 (m, 2H), 1.43-1.54 (m, 8H), 1.84 (quintet, J=7.8 Hz, 2H), 2.22 (t, J=7.2 Hz, 2H), 4.35 (t, J=7.4 Hz, 2H), 7.67-7.70 (m, 2H), 7.76-7.82 (m, 1H) and 7.85-7.88 (m, 1H). $^{13}$C NMR (D$_2$O) 21.6, 23.7, 25.2, 26.8, 33.4, 47.9, 54.6, 115.1, 125.1, 131.2, 136.5, 138.3, 141.7, 142.4, 178.7, 197.7.

5.5.a Synthesis of Fluorescent Compound 20

To a 100 mL flask were added 19 (0.41 g, 1.15 mmol), malonaldehyde dianilide hydrochloride (0.142 g, 0.55 mmol), acetic anhydride (5 mL) and sodium acetate (0.13 g). The mixture was heated at 110° C. for 4.5 h and then cooled to rt. The volatile components were removed under vacuum to leave a tar that was dissolved in conc. HCl (20 mL). The solution was stirred for 3 h and then diluted by addition to water (500 mL). The mixture was loaded onto a column of C-18 reverse-phase silica gel (3×12 cm) in water. The column was eluted with water (approx. 1 L) to wash the compound onto the column and to remove the excess acid. Gradient elution from 0-40% methanol in water eluted the fluorescent compound. The fractions were evaporated in vacuo to leave a blue residue that was dissolved in 0.1 M sodium bicarbonate solution. The solution was filtered and then 1.0 M HCl was added dropwise to lower the pH to approx. 1. The mixture was stirred for 30 min and then the solid was filtered off, washed with 1.0 M HCl (2×2 mL) and water (2 mL), and dried under high vacuum to afford fluorescent compound 20 as a blue solid (0.23 g, 51%).

5.5.b Characterization of Fluorescent Compound 20

$^1$H NMR (D$_2$O+2% (v/v) 30% NaOD) 1.23-1.30 (m, 4H), 1.42-1.50 (m, 16H), 1.67 (quintet, J=7.3 Hz, 4H), 2.03 (t, J=7.5 Hz, 4H), 3.91 (t, J=7.4 Hz, 4H), 6.12 (d, J=13.6 Hz, 2H), 6.40 (t, J=12.5 Hz, 1H), 7.10 (dd, J=1.9 Hz and 8.3 Hz, 2H), 7.47-7.53 (m, 2H), 7.59 (d, J=11.5 Hz, 2H) and 7.83 (t, J=13.1 Hz, 2H). $^{13}$C NMR 25.7, 26.1, 26.7, 26.8, 37.4 43.9, 48.9, 103.5, 110.3, 110.4, 124.0, 124.1, 124.7, 130.6, 130.7, 133.1, 134.9, 140.9, 141.0, 143.3, 153.4, 173.5, 183.4.

Example 6

Preparation of 1-(5-carboxy-pentyl)-2-[3-(1-(5-carboxy-pentyl)-3,3-dimethyl-5-phosphono-1,3-dihydro-indol-2-ylidene)-propenyl]-3,3-dimethyl-5-phosphono-3H-indolium (21)

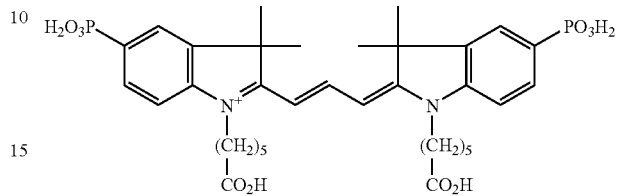

6.1.a Synthesis of Fluorescent Compound 21

To a 100 mL flask were added 19 (0.37 g, 1.04 mmol), diphenylformamidine (0.10 g, 0.5 mmol), sodium acetate (0.13 g, mmol) and acetic anhydride (5 mL). The mixture was heated at 110° C. for 4.5 h and then was cooled to rt. The volatile components were removed under vacuum to leave a tar that was dissolved in conc. HCl (20 mL). The solution was stirred for 3 h and then was diluted by addition to water (500 mL). The mixture was loaded onto a column of C-18 reverse-phase silica gel (3×12 cm) in water. The column was eluted with water (approx. 1 L) to wash the compound onto the column and to remove the excess acid. Gradient elution from 0-25% methanol in water eluted the fluorescent compound. The fractions were evaporated in vacuo to leave a red residue that was treated with a minimum of 20% water in methanol to dissolve the fluorescent compound. The solution was filtered and evaporated in vacuo. The residue was dried under high vacuum to afford fluorescent compound 21 (80 mg, 22%).

Example 7

Preparation of 1-(5-carboxy-pentyl)-2-[5-(1-ethyl-3,3-dimethyl-5-phosphono-1,3-dihydro-indol-2-ylidene)-penta-1,3-dienyl]-3,3-dimethyl-5-phosphono-3H-indolium (22)

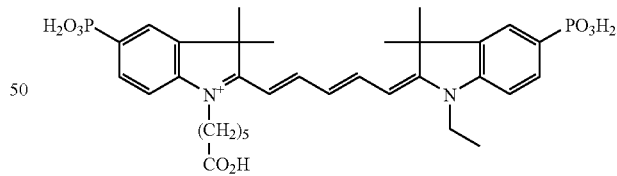

7.1.a Synthesis of Fluorescent Compound 22

To a 50 mL flask were added 6 (0.36 g, 1.34 mmol), malonaldehyde dianil hydrochloride (0.36 g, 1.40 mmol), acetic acid (4 mL) and acetic anhydride (4 mL). The mixture was heated at 110° C. for 90 min and then cooled to rt. The volatile components were removed under vacuum to leave a tar. The tar was dissolved in acetic acid (4 mL) and then pyridine (5 mL) and 19 (0.46 g, 1.30 mmol) were added. The mixture was heated at 110° C. for 3 h and was then cooled to rt. The volatile components were removed under high vacuum to leave a dark blue tar. The tar was dissolved in conc. HCl (30 mL). After stirring for 3 h the mixture was diluted with water (200 mL) and stirred for 30 min. The aqueous solution was filtered and loaded onto a column of C-18 reverse-phase silica gel (4×15 cm) in water. The column was eluted with water to remove the excess acid and then with a gradient of 0-45% methanol in water. The fractions were evaporated in vacuo to leave a blue residue that was taken up in a minimum of 20% methanol in water. The solution was filtered through a medium frit and then evaporated in vacuo to afford fluorescent compound 22 as a blue solid (0.205 g, 62%).

7.1.b Characterization of Fluorescent Compound 22

$^1$H NMR (CD$_3$OD) 1.39 (t, J=7.2 Hz, 3H), 1.44-1.54 (m, 2H), 1.65-1.90 (m, 16H), 2.31 (t, J=7.1 Hz, 2H), 4.10-4.20 (m, 4H), 6.27-6.35 (m, 2H), 6.64 (t, J=12.4 Hz, 1H), 7.26-7.30 (m, 2H), 7.83-7.91 (m, 4H) and 8.24-8.31 (m, 2H).

Example 8

Preparation of Fluorescent Compound 24

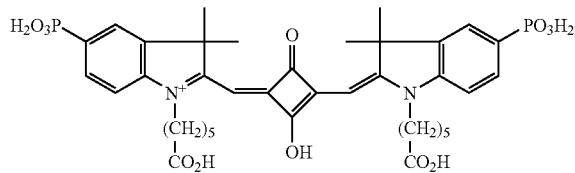

8.1.a Synthesis of Fluorescent Compound 24

To a 100 mL flask were added 19 (410 mg, 1.15 mmol), squaric acid (63 mg, 0.54 mmol), n-butanol (50 mL), and toluene (30 mL). The flask was fitted with a Dean Stark trap and the mixture was heated at reflux overnight. After cooling to rt, the solid was filtered off, washed with DCM (3×30 mL) and dried. The solid was dissolved in 0.2 M potassium carbonate solution (150 mL) and the solution was stirred for 6 days. 1.0 M HCl was added to lower the pH to approx 1-2. A suspension formed that was stirred for another hour. The solid was filtered off and was washed with water (2×3 mL). The solid was dried under vacuum to afford fluorescent compound 24 as a blue solid (0.32 g, 72%).

8.1.b Characterization of Fluorescent Compound 24

$^1$H NMR (D$_6$-DMSO) 1.35-1.42 (4H, m), 1.56 (quintet, J=7.3 Hz, 4H), 1.65-1.75 (m, 16H), 2.21 (t, J=7.2 Hz, 4H), 4.07-4.14 (m, 4H), 5.85 (s, 2H), 7.39-7.4 (m, 2H), 7.63-7.69 (m, 2H), 7.73 (d, J=11.8 Hz, 2H). $^{13}$C NMR 24.7, 26.4, 26.8, 27.0, 34.0, 43.6, 49.2, 87.5, 110.6, 124.8, 128.6, 130.4, 131.6, 141.5, 144.9, 169.9, 174.9, 180.2, 181.1.

Example 9

Preparation of Fluorescent Compound 26

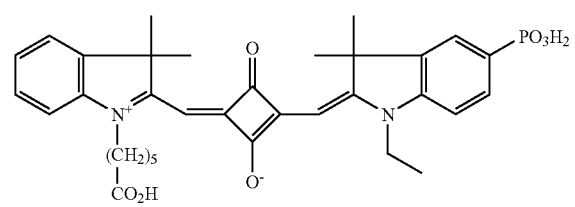

9.1.a Synthesis of Fluorescent Compound 26

To a 250 mL flask were added 7 (0.46 g, 1.14 mmol), dibutylsquarate (0.26 g, 1.14 mmol), ethanol (80 mL), and triethylamine (1.70 mL). The mixture was heated at reflux for 18 h and then 1.0 M aqueous sodium hydroxide (2.5 mL) was added. Heating was continued for 1 h. The mixture was cooled to rt, 1.0 M HCl was added and then the mixture was evaporated to dryness in vacuo to afford 25 as a yellow-brown wax. Butanol (50 mL), toluene (50 mL) and 6 (0.30 g, 1.12 mmol) were added. The flask was fitted with a Dean Stark trap and the mixture was heated at reflux for 6 days. The volatile components were removed in vacuo and the residue was dissolved in 100 mL of 1.0 M potassium carbonate solution. The mixture was stirred at rt for 4 days and then 1.0 M HCl was added to lower the pH to approx 1-2. A suspension formed that was stirred for a further 1 h. The solid was filtered off and washed with 1.0 M HCl (10 mL). After air drying, the solid was washed with DCM (5×30 mL). The solid was dissolved in 0.1 M potassium carbonate solution (100 mL) and the solution was loaded onto a column of C-18 reverse-phase silica gel (3×12 cm) in water. The column was eluted with water (200 mL) to remove the salts and excess base, with 0.5 M HCl (100 mL) to generate the free acid of the fluorescent compound and then with water to remove the excess acid. Gradient elution from 0-45% methanol in water first eluted the symmetrical bisphosphonic acid fluorescent compound and then fluorescent product 26. The fractions were evaporated in vacuo to leave a blue residue that was taken up in methanol (100 mL) and filtered through a medium frit. The solvent was removed in vacuo to afford fluorescent compound 26 as a blue solid (0.060 g, 9%).

9.1.b Characterization of Fluorescent Compound 26

$^1$H NMR (D$_6$-DMSO) 1.22-1.30 (m, 2H), 1.35-1.43 (m, 2H), 1.53-1.75 (m, 16H), 2.19 (t, J=7.1 Hz, 2H), 4.05-4.17 (m, 4H), 5.78 (s, 2H), 7.14 (t, J=7.0 Hz, 1H) 7.18-7.24 (m, 1H), 7.28-7.37 (m, 2H), 7.50 (d, J=7.3 Hz, 1H), 7.66-7.75 (m, 1H)

Example 10

Preparation of 5-carboxymethyl-1-ethyl-2-[5-(1-ethyl-3,3-dimethyl-5-phosphono-1,3-dihydro-indol-2-ylidene)-penta-1,3-dienyl]-3,3-dimethyl-3H-indolium (30)

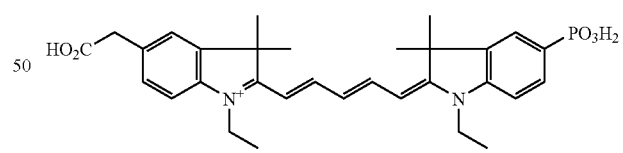

Compounds 27 and 28 were prepared by methods described in Southwick et al., *Cytometry,* 1990, 11, 418-430.

10.1.a Synthesis of Fluorescent Compound 30

To a 50 mL flask were added 28 (0.387 g, 1.04 mmol), malonaldehyde dianilide hydrochloride (0.321 g, 1.24 mmol), acetic acid (5 mL) and acetic anhydride (5 mL). The mixture was heated at 110° C. for 1 h and was then cooled to rt. The volatile components were removed under vacuum to leave a tar consisting of 29. The tar was washed with ether (2×60 mL). The tar was dissolved in acetic acid (5 mL) and then pyridine (10 mL) and compound 6 (0.27 g, 1.0 mmol) were added. The mixture was heated at 110° C. for 1 h and then cooled to rt. The volatile components were removed in vacuo and the residue was dissolved in conc. HCl (30 mL). After stirring for 3 h, the mixture was diluted with water (300 mL) and then basified, first by addition of 4 M sodium hydroxide solution until the pH was approx. 4 and then with saturated sodium bicarbonate solution. The fluorescent product initially precipitated from the mixture but then it re-dissolved. The aqueous solution was loaded onto a column of C-18 reverse-phase silica gel (4×15 cm) in water. The column was eluted with water to remove salts and excess base, then with 1 M HCl to generate the free acid of the fluorescent compound and then again with water to remove the excess acid. Gradient elution from 0-60% methanol in water first gave a small amount of the symmetrical bisphosphonic acid fluorescent compound, then fluorescent compound 30. The product containing fractions were evaporated in vacuo to leave a blue residue that was taken up in methanol (20 mL). The solution was filtered through a medium frit and evaporated in vacuo to afford fluorescent compound 30 as a blue solid (0.176 g, 31%).

10.1.b Characterization of Fluorescent Compound 30

$^1$H NMR (CD$_3$OD) 1.32-1.41 (m, 6H), 1.72 (s, 6H), 1.73 (s, 6H), 3.70 (s, 2H), 4.10-4.20 (m, 4H), 6.26 (d, J=13.6 Hz, 1H), 6.33 (d, J=14.0 Hz, 1H), 6.62 (t, J=12.4 Hz, 1H), 7.24-7.29 (m, 2H), 7.34-7.37 (m, 1H), 7.45 (d, J=1.4 Hz, 1H), 7.83-7.90 (m, 2H) and 8.21-8.30 (m, 2H). $^{13}$C NMR 11.2, 11.3, 26.4, 26.5, 38.5, 38.9, 40.3, 49.0, 49.4, 102.5, 103.3, 109.3, 109.5, 110.5, m 123.4, 124.5, 124.6, 125.4, 129.7, 131.4, 131.5, 132.6, 140.4, 140.6, 141.8, 143.0, 154.0, 154.6, 172.5, 173.6, 174.1.

Example 11

Preparation of 5-carboxymethyl-1-ethyl-2-[3-(1-ethyl-3,3-dimethyl-5-phosphono-1,3-dihydro-indol-2-ylidene)-propenyl]-3,3-dimethyl-3H-indolium (31)

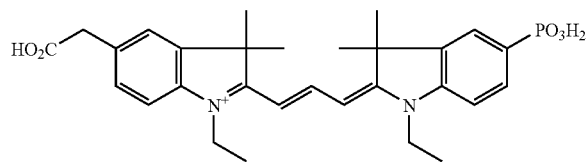

11.1.a Synthesis of Fluorescent Compound 31

To a 100 mL flask were added 6 (0.29 g, 1.08 mmol), diphenylformamidine (0.40 g, 2.0 mmol), acetic acid (5 mL) and acetic anhydride (5 mL). The mixture was heated at 120° C. for 3 h and was then cooled to rt. The volatile components were removed under vacuum to leave a tar that was washed with ether (2×30 mL) and ethyl acetate (2×50 mL) to afford 8. The solid was dissolved in acetic acid (5 mL) and then pyridine (8 mL) and 28 (0.370 g, 1.0 mmol) were added. The mixture was heated at 120° C. for 3 h and then cooled to rt. The volatile components were removed in vacuo and the residue was dissolved in conc. HCl. After stirring for 3 h the mixture was diluted with water (200 mL) and then basified, first by addition of 4 M sodium hydroxide solution until the pH was approx. 4 and then with saturated sodium bicarbonate solution. The fluorescent compound initially precipitated from the mixture but then re-dissolved. The aqueous solution was loaded onto a column of C-18 reverse-phase silica gel (3×15 cm) in water. The column was eluted with water to remove salts and excess base, then with 1 M HCl to generate the free acid of the fluorescent compound and finally with water to remove the excess acid. Gradient elution from 0-55% methanol in water (5% steps of 500 mL-1 L) first eluted the symmetrical bisphosphonic acid fluorescent compound and then the unsymmetrical fluorescent compound. The product containing fractions were evaporated in vacuo to leave a red residue that was taken up in methanol and filtered through a medium frit. The methanol was removed in vacuo to afford fluorescent compound 31 as a red solid (0.072 g, 14%).

11.1.b Characterization of Fluorescent Compound 31

$^1$H NMR (CD$_3$OD) 1.40-1.46 (m, 6H), 1.78 (s, 6H), 1.79 (s, 6H), 3.73 (s, 2H), 4.18-4.30 (m, 4H), 6.48 (d, J=13.2 Hz, 1H), 6.58 (d, J=13.6 Hz, 1H), 7.38-7.44 (m, 3H), 7.53 (s, 1H), 7.85-7.91 (m, 2H) and 8.57 (t, J=13.4 Hz, 1H). $^{13}$C NMR 11.1, 11.5, 26.7, 27.0, 38.9, 39.5, 40.1, 48.9, 49.8, 102.0, 103.6, 110.2, 110.4, 111.3, 123.6, 124.5, 124.6, 127.4, 129.3, 130.0, 131.9, 132.1, 133.5, 140.4, 140.6, 140.7, 141.6, 144.6, 151.2, 173.6, 173.8, 175.6.

Example 12

Preparation of 2-(2-{2-chloro-3-[2-(1-(5-carboxy-pentyl)-3,3-dimethyl-5-phosphono-1,3-dihydro-indol-2-ylidene)-ethylidene]-cyclohex-1-enyl}-vinyl)-1-(5-carboxy-pentyl)-3,3-dimethyl-5-phosphono-3H-indolium (33)

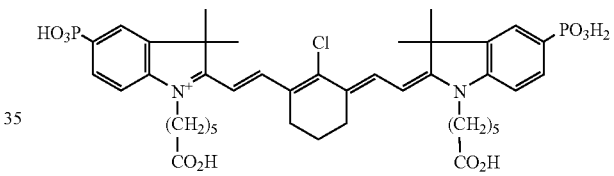

12.1.a Synthesis of 2-chloro-3-hydroxymethylene-cyclohex-1-enecarbaldehyde (32)

To a 500 mL flask were added DCM (40 mL) and DMF (40 mL). The mixture was cooled in an ice bath and then a solution of phosphorus oxychloride (37 mL) in DCM (35 mL) was added dropwise over approx. 1 h. To the still cool reaction mixture was added cyclohexanone (10 g, 0.10 mol) dropwise over 20 min. The mixture was stirred for a further 10 min and then was then heated at reflux for 3.5 h. After cooling to rt the mixture was poured onto 200 g of ice and then stirred until the ice melted. The mixture was left to stand during which time the aqueous phase became hot and caused some of the DCM to boil off. After the mixture cooled, crystals formed in the mixture. These were filtered off, washed with water (2×20 mL) and dried under vacuum to afford 32 (6.0 g, 34%).

12.2.a Synthesis of Fluorescent Compound 33

To a 100 mL flask were added 19(0.402 g, 1.13 mrnol), 32(0.095 g, 0.55 mmol), n-butanol (50 mL), and toluene (30 mL). The flask was fitted with a Dean Stark trap and the mixture was heated at reflux overnight. After cooling to rt, the solid was filtered off, washed with DCM (3×30 mL) and dried. The solid was dissolved in 0.1 M potassium carbonate solution (100 mL) and the solution was stirred for 36 h. 1.0 M HCl was added to lower the pH to approx 1-2. A suspension formed that was stirred for a further 1 h. The solid was filtered off and was washed with water (3×2 mL). The solid was dried under vacuum to afford fluorescent compound 33 as a green solid (0.305 g, 63%).

12.2.b Characterization of Fluorescent Compound 33

$^1$H NMR (D$_2$O+2% (v/v) 30% NaOD) 1.04 (t, J=7.2 Hz, 6H), 1.24-1.32 (m, 4H), 1.47 (quintet, J=7.4 Hz, 4H), 1.59 (s, 12H), 1.69 (quintet, J=7.3 Hz, 4H), 2.03 (t, J=7.5 Hz, 4H), 3.68 (quintet, J=7.2 Hz, 4H), 3.94 (t, J=7.4 Hz, 4H), 6.22 (d, J=13.4 Hz, 2H), 7.22 (dd, J=1.3 Hz and 8.1 Hz, 2H), 7.58-7.65 (m, 4H) and 8.38 (t, J=13.1 Hz, 2H). $^{13}$C NMR 20.5, 25.6, 25.9, 26.1, 26.6, 27.3, 44.1, 49.2, 101.2, 110.4, 110.5, 124.2, 124.3, 127.0, 130.8, 130.9, 134.9, 136.6, 140.6, 140.7, 142.9, 143.6, 149.1, 172.9, 183.3.

Example 13

Preparation of 2-(2-{2-chloro-3-[2-(1-ethyl-3,3-dimethyl-5-phosphono-1,3-dihydro-indol-2-ylidene)-ethylidene]-cyclohex-1-enyl}-vinyl)-1-ethyl-3,3-dimethyl-5-phosphono-3H-indolium (34)

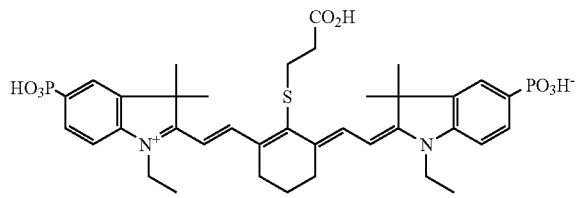

13.1.a Synthesis of Fluorescent Compound 34

To a 250 mL flask were added 6 (0.940 g, 3.51 mmol), 32 (0.36 g, 2.1 mmol), n-butanol (120 mL), and toluene (60 mL). The flask was fitted with a Dean Stark trap and the mixture was heated at reflux for 18 h. The toluene was removed by distillation and then the mixture was cooled to 80° C. DIEA (1.2 mL) and 3-mercaptopropionic acid (0.40 mL) were added and heating was continued for 2 h. The butanol was removed in vacuo and the residue was washed with ether (2×200 mL) to give a fine powder that was filtered off. The solid was dissolved in 50 mL of carbonate/bicarbonate buffer pH 9.5 and then 1 M hydrochloric acid was added drop wise to the stirring solution to precipitate the fluorescent compound. The solid was filtered off and was washed with water (3×10 mL). The solid was dried and was then added to methanol (80 mL). After stirring for 20 min the solid was filtered off and was washed with methanol until the washings were pale blue in color. The solid was dried under vacuum to afford fluorescent compound 34 as a green solid (0.82 g, 63%).

Example 14

Preparation of 5-aminomethyl-1-ethyl-2-[5-(1-ethyl-3,3-dimethyl-5-phosphono-1,3-dihydro-indol-2-ylidene)-penta-1,3-dienyl]-3,3-dimethyl-3H-indolium (40)

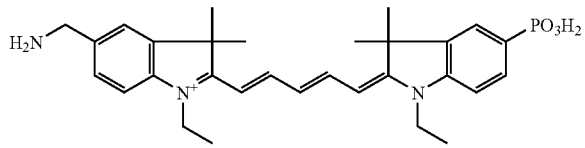

14.1.a Synthesis of C-(2,3,3-trimethyl-3H-indol-5-yl)-methylamine (36)

Compound 36 was prepared according to *Australian J. Chem.*, 1970, 30, 689.

14.2.a Synthesis of N-(2,3,3-trimethyl-3H-indol-5-ylmethyl)-formamide (37)

Aminomethylindole 36 (1.29 g, 6.86 mmol) was dissolved in methyl formate (40 mL) and the mixture was heated at reflux for 2 days. The volatile components were evaporated in vacuo to afford the protected amine 37 as a pale yellow oil (1.40 g, 95%).

14.2.b Characterization of N-(2,3,3-trimethyl-3H-indol-5-yl-methyl)-formamide (37)

$^1$H NMR (D$_6$-DMSO) 1.20 (s, 6H), 2.18 (s, 3H), 4.37 and 4.42 (2x d, J=6 Hz, 2H), 6.81 and 6.48 (2×s, 1H), 7.11-7.16 (m, 2H), 7.32-7.40 (m, 1H), 8.18 (s, 1H). $^{13C\ NMR}$ 15.4, 23.1, 42.1, 45.8, 53.7, 119.8, 121.1, 127.3, 134.7, 146.4, 153.1, 164.8, 188.7.

14.3.a Synthesis of 1-ethyl-5-formylaminomethyl-2,3,3-trimethyl-3H-indolium (38)

Compound 37 (2.40 g, 11.1 mmol) was dissolved in acetonitrile (20 mL) and ethyl iodide (8 mL) was added. The mixture was heated at reflux overnight and then the volatile components were removed in vacuo. The residue was dissolved in methanol (3 mL) and this solution was added dropwise to stirred ether 100 mL. After stirring for 1.5 h the solid was filtered and then washed with ether to afford 38 as a pale pink solid (3.6 g, 87%).

14.3.b Characterization of 1-ethyl-5-formylaminomethyl-2,3,3-trimethyl-3H-indolium (38)

$^1$H NMR (D$_6$-DMSO) 1.43 (t, J=7.3 Hz, 3H), 1.52 (s, 6H), 2.84 (s, 3H), 4.42 (d, J=6.1 Hz, 2H), 4.48 (quartet, J=7.0 Hz, 2H), 7.48-7.51 (m, 1H), 7.72 (d, J=1.1 Hz, 1H), 7.94 (d, J=8.4 Hz, 1H), 8.62 (t, J=5.3 Hz, 1H). $^{13}$C NMR 13.3, 13.5, 22.5, 41.0, 43.7, 54.6, 115.8, 122.8, 128.3, 140.2, 141.5, 142.7, 161.8, 196.2.

14.4.a Synthesis of Fluorescent Compound 39

To a 100 mL flask were added 6 (0.50 g, 1.87 mmol), malonaldehyde dianilide hydrochloride (0.50 g, 1.93 mmol), acetic acid (10 mL) and acetic anhydride (10 mL). The mixture was heated at 110° C. for 2.5 h and was then cooled to rt. The volatile components were removed under vacuum to leave a tar. The tar was washed with ether (2×40 mL), and was dissolved in acetic acid (4 mL). Pyridine (5 mL) and 38 (0.75 g, 2.0 mmol) were added. The mixture was heated at 110° C. for 1 h and was then cooled to rt. The volatile components were removed under high vacuum to leave a dark blue tar that was dissolved in conc. HCl (30 mL). After stirring for 3 h the mixture was diluted with water (250 mL) and then basified, first by addition of 4 M sodium hydroxide solution until the pH was approx. 4 and then with saturated sodium bicarbonate solution. The fluorescent product initially precipitated from the mixture but then re-dissolved. The aqueous solution was loaded onto a column of C-18 reverse-phase silica gel (4×15 cm) in water. The column was eluted with water to remove the salts and excess base, then with 1.0 M HCl to generate the free acid of the fluorescent compound and finally with water to remove the excess acid. Gradient elution from 0-55% methanol in water (5% steps of 500 mL-1 L) first eluted the symmetrical bisphosphonic acid fluorescent compound and then fluorescent compound 39. The product containing fractions were evaporated in vacuo to leave a blue residue that was taken up in methanol (40 mL) and filtered through a medium frit. The methanol was removed in vacuo to afford fluorescent compound 39 as a blue solid (0.47 g, 46%).

14.4.b Characterization of Fluorescent Compound 39

$^1$H NMR (CD$_3$OD) 1.36-1.40 (m, 6H), 1.73 (s, 12H), 4.12-4.18 (m, 4H), 4.74 (s, 2H) 6.27-6.32 (m, 2H), 6.62 (t, J=12.4 Hz, 1H), 7.25-7.29 (m, 2H), 7.36-7.39 (m, 1H), 7.46 (d, J=1.2 Hz, 1H), 7.83-7.90 (m, 2H) 7.18 (s, 1H) and 8.22-8.30 (m, 2H). $^{13}$C NMR 11.2, 11.3, 26.4, 26.4, 38.6, 38.8, 41.1, 49.0, 49.3, 102.7, 103.1, 109.4, 109.6, 110.6, 121.7, 124.6, 124.7, 125.5, 128.0, 131.4, 131.5, 133.4, 135.2, 135.9, 140.5, 140.6, 141.0, 142.0, 142.9, 154.2, 154.5, 162.4, 172.9, 173.6.

14.5.a Synthesis of Fluorescent Compound 40

To a 50 mL flask were added fluorescent compound 39 (0.39 g, 0.713 mmol), methanol (100 mL) and conc. HCl (10 mL). The mixture was stirred at rt for 40 hours. The mixture was diluted with water (200 mL) and then basified by addition of saturated sodium bicarbonate solution. The aqueous solution was loaded onto a column of C-18 reverse-phase silica gel (3×10 cm) in water. The column was eluted with water to remove the salts and excess base, then with 1.0 M HCl (50 mL) and finally water (500 mL) to remove the excess acid. Gradient elution from 0-75% methanol in water (12.5% steps of 100 mL-500 mL) first eluted residual starting material and then fluorescent compound 40. The fractions were evaporated in vacuo to leave a blue residue that was taken up in methanol (10 mL) and filtered through a medium frit. The methanol was removed in vacuo to afford fluorescent compound 40 as a blue solid (0.266 g, 72%).

Example 15

Preparation of Fluorescent Compound 42, Sodium Salt

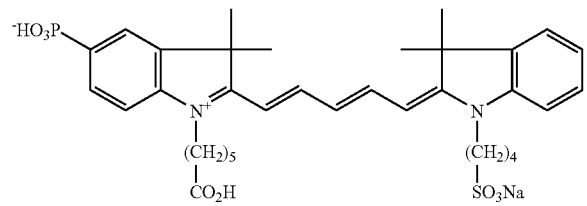

15.1.a Synthesis of Indolium Salt 41

Indolium salt 41 was prepared by methods in the cited literature.

15.2.a Synthesis of Fluorescent Compound 42

To a 250 mL flask were added indolium salt 41 (0.60 g, 2.04 mmol), malonaldehyde dianil (0.60 g, 2.3 mmol), acetic acid (25 mL) and acetic anhydride (25 mL). The mixture was heated at 115° C. for 2 hours, cooled to room temperature and then the volatile components were removed under vacuum. The residue was washed with ethyl acetate (3×100 mL) to give a powder. To the powder were added indolium salt 19 (0.70 g, 2.0 mmol), and acetic acid (25 mL). The mixture was warmed until the solids dissolved and then pyridine (35 mL) was added. The mixture was heated to 115° C. for 3 hours during which time the mixture became deep blue. The mixture was cooled to room temperature and the volatile components were removed under vacuum. The residue was treated with saturated aqueous sodium bicarbonate solution (250 mL) and the resulting solution was filtered. The solution was loaded onto a column of C-18 reverse-phase silica gel (4×20 cm) in water. The column was eluted with water (approx. 200 mL), 0.5 M HCl (approx. 500 mL) and then with gradient elution from 0-30% methanol in TEA/acetic acid buffer (5% steps of 500 mL-1 L). The product containing fractions were evaporated in vacuo to leave a blue residue that was dissolved in 1.0 M HCl (approx. 100 mL). The solution was loaded onto a column of C-18 reverse-phase silica gel (3×10 cm) in water and then the column was eluted with 1.0 M hydrochloric acid (200 mL) and then with water until the pH of the effluent was neutral. The fluorescent compound was eluted using a sharp gradient of 0-50% methanol in water. The fractions were evaporated in vacuo to afford fluorescent compound 42 as a blue solid (0.95 g, 69%).

15.3.a Synthesis of Fluorescent Compound 42, Sodium Salt

Fluorescent compound 42 (0.50 g) was dissolved in a mixture of DI water (200 mL) and methanol (50 mL). The solution was passed through a column (2.5×10 cm) of DOWEX® 50-8X anion exchange resin, sodium form. After washing the remaining fluorescent compound off the column with DI water the aqueous solution was concentrated to approx. 20 mL. The solution was filtered through a medium frit and was then evaporated under vacuum to afford the sodium salt of fluorescent compound 42 as a blue solid.

Example 16

Preparation of Fluorescent Compound 43, Sodium Salt

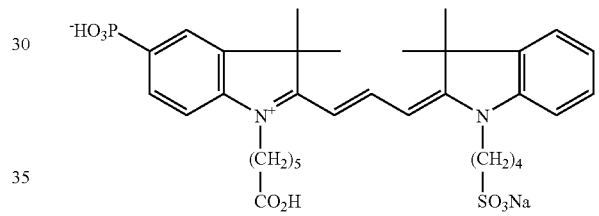

16.1.a Synthesis of Fluorescent Compound 43

To a 250 mL flask were added indolium salt 41 (0.60 g, 2.04 mmol), diphenylformamidine (0.50 g, 2.6 mmol), acetic acid (21 mL) and acetic anhydride (15 mL). The mixture was heated at 115° C. for 3 hours, was cooled to room temperature and then the volatile components were removed under vacuum. The residue was washed with ethyl acetate (3×100 mL) to give a powder. To the powder were added indolium salt 19 (0.70 g, 2.0 mmol), and acetic acid (25 mL). The mixture was warmed until the solids dissolved and then pyridine (35 mL) was added. The mixture was heated to 115° C. for 30 min and then acetic anhydride (15 ml) was added. The mixture was heated for a further 2 hours during which time the mixture became deep red. The mixture was cooled to room temperature and then the volatile components were removed under vacuum. The residue was treated with saturated aqueous sodium bicarbonate solution (250 mL). The solution was filtered and loaded onto a column of C-18 reverse-phase silica gel (4×20 cm) in water. The column was eluted with water (approx. 200 mL), 0.5 M HCl (approx. 500 mL) and then with gradient elution from 0-30% methanol in TEA/acetic acid buffer (5% steps of 500 mL-1 L). The fractions were evaporated in vacuo to leave a red residue that was dissolved in 1 M HCl (approx. 100 mL). The solution was loaded onto a column of C-18 reverse-phase silica gel (3×10 cm) in water and then the column was eluted with 1.0 M hydrochloric acid (200 mL) and then with water until the pH of the effluent was neutral. The fluorescent compound was eluted using a sharp gradient of 0-50% methanol in water. The product containing fractions were evaporated in vacuo to afford fluorescent compound 43 as a red solid (0.45 g, 34%).

16.2.a Synthesis of Fluorescent Compound 43, Sodium Salt

Fluorescent compound 43 (0.40 g) was dissolved in a mixture of DI water (200 mL) and methanol (50 mL). The solution was passed through a column (2.5×10 cm) of DOWEX® 50-8X anion exchange resin, sodium form. After washing the remaining fluorescent compound off the column with DI water the aqueous solution was concentrated to approx. 20 mL. The solution was filtered through a medium fit and was then evaporated under vacuum to afford the sodium salt of fluorescent compound 43 as a red solid.

Example 17

Preparation of N-Hydroxy Succinimidyl Ester of 9

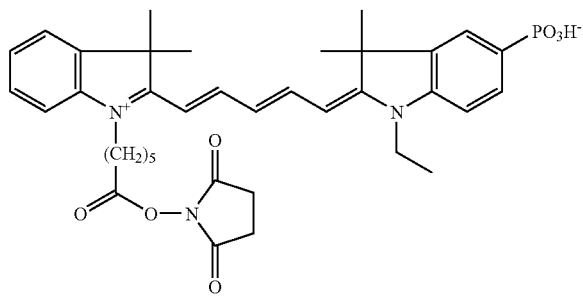

17.1.a Synthesis of 9-OSu

To a 25 mL flask were added fluorescent compound 9 (0.093 g, 0.163 mmol), water (0.7 mL) and DMF (1.4 mL). The mixture was stirred until the solid dissolved and then DIEA (0.20 mL) and DMF (4.9 mL) were added. After stirring for 10 min TSTU (0.050 g, 0.166 mmol) was added. Stirring was continued for 1 h and then the volatile components were removed under high vacuum without heating. The residue was dissolved in DCM and the solution was filtered through a medium frit. The DCM was evaporated in vacuo without heating and the residue was dried under high vacuum overnight with phosphorus pentoxide to afford fluorescent compound 9-OSu as a dark blue solid (137 mg)

Example 18

Preparation of N-Hydroxy Succinimidyl Ester of 11

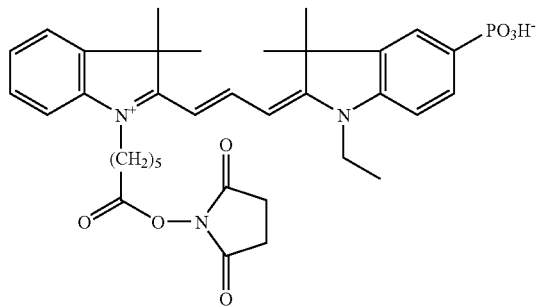

18.1.a Synthesis of 11-OSu

To a 25 mL flask were added fluorescent compound 11 (0.0895 g, 0.161 mmol), water (0.7 mL) and DMF (1.4 mL). The mixture was stirred until the solid dissolved and then DIEA (0.24 mL) and DMF (4.8 mL) were added. After stirring for 10 min TSTU (0.0503 g, 0.167 mmol) was added. Stirring was continued for 1 h and then the volatile components were removed under high vacuum without heating. The residue was dissolved in DCM and the solution was filtered through a medium frit. The DCM was evaporated in vacuo without heating and the residue was dried under high vacuum overnight with phosphorus pentoxide to afford fluorescent compound 11-OSu as a dark red solid (147 mg)

Example 19

Preparation of N-Hydroxy Succinimidyl Ester of 13

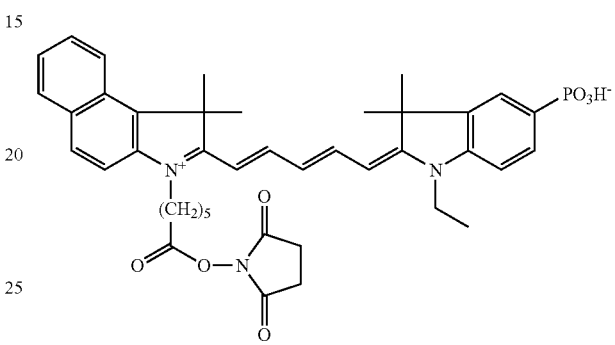

19.1.a Synthesis of 13-OSu

To a 50 mL flask were added fluorescent compound 13 (0.050 g), DMF (2.5 mL), water (0.25 mL), and DIEA (0.060 mL). The mixture was stirred for 30 min and then TSTU (0.029 g) was added. After stirring for another hour the volatile components were removed under high vacuum without heating. The solid residue was washed with THF (2×15 mL) and was then dissolved in DCM (60 mL). The solution was washed with 0.1N HCl (1×10 mL), dried (MgSO$_4$) and then evaporated in vacuo to afford 13-OSu as a blue solid.

Example 20

Preparation of N-Hydroxy Succinimidyl Ester of 42

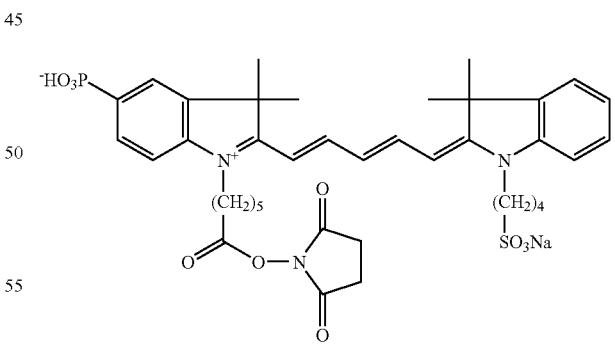

20.1.a Synthesis of 42-OSu

To a 50 mL flask were added fluorescent compound 42 (0.095 g, 0.161 mmol), water (0.7 mL) and DMF (1.4 mL). The mixture was stirred until the solid dissolved and then DIEA (0.14 mL) and DMF (2.8 mL) were added. After stirring for 10 min TSTU (0.060 g, 0.20 mmol) was added. Stirring was continued for 1 h and then the volatile components were removed under high vacuum without heating. The residue was washed with DCM (3×30 mL) to afford a solid. The solid was filtered off, was washed with acetonitrile (3×20 mL) and was dried under high vacuum overnight with phosphorus pentoxide to afford 42-OSu as a dark blue solid (101 mg).

Example 21

Preparation of N-Hydroxy Succinimidyl Ester of 43

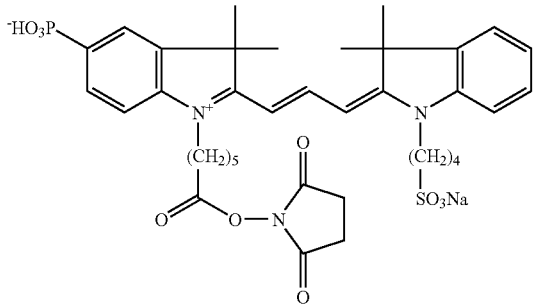

21.1.a Synthesis of 43-OSu

To a 50 mL flask were added fluorescent compound 43 (0.1025 g, 0.150 mmol), water (0.8 mL) and DMF (1.8 mL). The mixture was stirred until the solid dissolved and then DIEA (0.16 mL) and DMF (3.6 mL) were added. After stirring for 10 min TSTU (0.070 g, 0.23 mmol) was added. Stirring was continued for 1 h and then the volatile components were removed under high vacuum without heating. The residue was washed with DCM (3×30 mL) to afford a solid. The solid was filtered off, washed with acetonitrile (3×20 mL) and dried under high vacuum overnight with phosphorus pentoxide to afford 43-OSu as a dark red solid (109 mg).

Example 22

Methods for Labeling Proteins with Fluorescent Succinimidyl Esters of the Compounds of the Invention 22.1.a Method 1

A stock solution of the protein sheep-gamma-globulin was prepared at a concentration of 2 mg/mL (approx. $1.33 \times 10^{-5}$ M) in a 0.1 M sodium bicarbonate solution. 1 mL aliquots of the stock were dispensed into vials. Stock solutions of the active esters 9-OSu, 11-OSu, 13-OSu, 42-OSu and 43-OSu were prepared at a concentration of 0.01 M in DMSO. Aliquots of the active ester stock solutions were added to the protein to afford a series of starting compound to protein ratios ranging from 0.7:1 to 50:1. The solutions were mixed well and left to stand at rt overnight. The samples were filtered and then loaded onto a SEPHADEX® G50 gel column (0.7× 12 cm) which was eluted with PBS (pH 7.3). The labeled proteins, which eluted from the column prior to the hydrolyzed fluorescent compounds were studied without further purification.

22.2.a Method 2

Each succinimidyl ester was added to a 1.5 mL EPPENDORF® microcentrifuge tube. Solutions of SGG (1 mg/mL, approx. $1.5 \times 10^{-5}$ M) in a 0.1 M sodium bicarbonate solution were added to the fluorescent compounds in the tube and the mixtures were shaken until the fluorescent compounds dissolved completely. The mixtures were left to stand at rt overnight. The samples were filtered and then loaded onto a SEPHADEX® G50 gel column (0.7×12 cm), which was then eluted with PBS (pH 7.3). The labeled proteins were collected ahead of the hydrolyzed fluorescent compounds and were studied without further purification.

Example 23

23.1.a Method for Labeling Oligonucleotides with Fluorescent Succinimidyl Esters A $T_{10}$ DNA oligonucleotide was prepared using standard automated synthesis regimes on a BIOSEARCH® 8700 Oligonucleotide synthesizer. A MMT protected amino functionalized amidite was manually coupled to the DNA fragment. The protecting group was removed to afford the amino-modified oligonucleotides still attached to the CPG. The CPG (approx. 0.01 g) was suspended in a DMSO solution (0.30 mL) of the active ester 11-OSu (1.0 mg/0.1 mL) and N-methylmorpholine (0.020 mL). The DNA was cleaved from the solid support using concentrated aqueous ammonia at 60° C. for 2 hours. After removal of the volatile components using a speed vac, the labeled oligo-nucleotides were isolated by a combination of AX and RP HPLC to afford the labeled oligonucleotides.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A fluorescent compound comprising a structure according to the Formula:

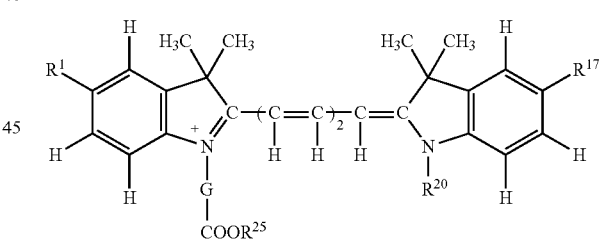

wherein $R^1$ and $R^{17}$ are each independently $P(O)(OR^{30})(OR^{30})$, wherein each $R^{30}$ is independently selected from H, a negative charge, and a salt counterion;

$R^{20}$ is unsubstituted alkyl;

G is unsubstituted alkyl;

$R^{25}$ is a member selected from H, a negative charge, a salt counterion, a reactive functional group, a solid support and a carrier molecule.

2. The fluorescent compound of claim 1 wherein $R^{20}$ is unsubstituted $C^1$-$C^4$ alkyl.

3. The fluorescent compound of claim 2 wherein $R^{20}$ is ethyl.

4. The fluorescent compound of claim 1 wherein G is —$(CH_2)_5$—.

5. The fluorescent compound of claim 2 wherein G is —$(CH_2)_5$—.

6. The fluorescent compound of claim 3 wherein G is —(CH$_2$)$_5$—.

7. The fluorescent compound of claim 1 wherein R$^{25}$ is —NR$^{35}$R$^{36}$ wherein R$^{35}$ and R$^{36}$ are independently selected from substituted or unsubstituted alkyl, substituted or unsubstituted heteroalkyl, substituted or unsubstituted heterocycloalkyl, substituted or unsubstituted aryl and substituted or unsubstituted heteroaryl; and R$^{35}$ and R$^{36}$, together with the nitrogen to which they are bound, are optionally joined to form a ring system.

8. The fluorescent compound of claim 1 wherein R$^{25}$ is

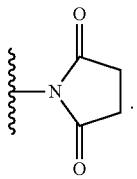

9. The fluorescent compound of claim 1, having a structure selected from

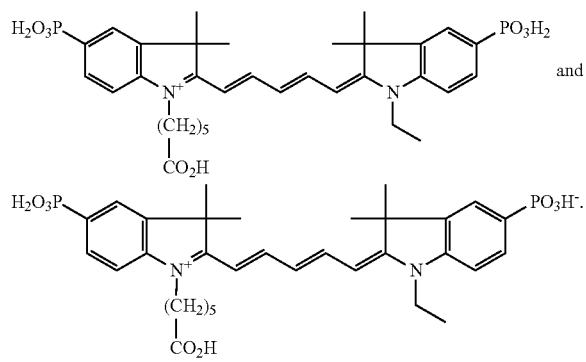

10. The fluorescent compound of claim 1, having a structure selected from

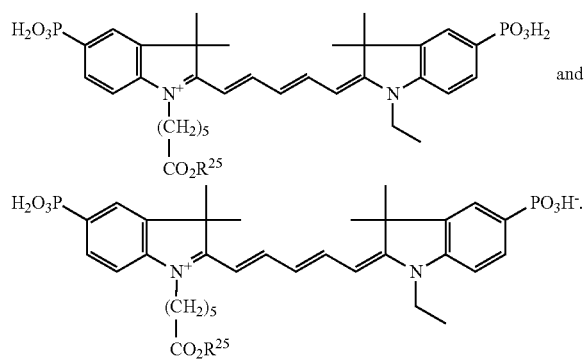

11. The fluorescent compound of claim 10 wherein R$^{25}$ is selected from a reactive functional group, a solid support and a carrier molecule.

12. The fluorescent compound of claim 11 wherein R$^{25}$ is a reactive functional group.

13. The fluorescent compound of claim 10 wherein R$^{25}$ is —NR$^{35}$R$^{36}$ wherein R$^{35}$ and R$^{36}$ are members independently selected from substituted or unsubstituted alkyl, substituted or unsubstituted heteroalkyl, substituted or unsubstituted heterocycloalkyl, substituted or unsubstituted aryl and substituted or unsubstituted heteroaryl; and R$^{35}$ and R$^{36}$, together with the nitrogen to which they are bound, are optionally joined to form a ring system.

14. The fluorescent compound of claim 10 wherein R$^{25}$ is

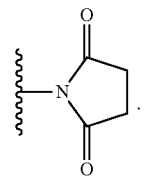

15. The fluorescent compound of claim 11 wherein R$^{25}$ is a solid support.

16. The fluorescent compound of claim 11 wherein R$^{25}$ is a carrier molecule.

17. The fluorescent compound of claim 16 wherein the carrier molecule is a nucleic acid or a protein.

18. The fluorescent compound of claim 1 wherein said carrier molecule further comprises a quencher moiety.

19. The fluorescent compound of claim 18 wherein said fluorescent compound, together with said quencher moiety, comprise a donor-acceptor energy transfer pair.

20. The fluorescent compound of claim 19 wherein said quencher moiety has substantially no native fluorescence.

21. The fluorescent compound of claim 19, wherein said quencher moiety comprises at least three residues wherein each of said residues is independently selected from substituted or unsubstituted aryl and substituted or unsubstituted heteroaryl, and at least two of said residues are covalently linked via an exocyclic diazo bond.

22. The fluorescent compound of claim 1, wherein said fluorescent compound further comprises a nucleic acid at a position which is a member selected from the 3'-terminus, the 5'-terminus, a nucleobase, and a phosphorus-containing internucleotide bridge of said nucleic acid.

23. The fluorescent compound of claim 1, wherein said carrier molecule is a peptide comprising a cleavage recognition site for an enzyme.

24. The fluorescent compound of claim 1, wherein said fluorescent compound further comprises a member selected from a protein, saccharide, nucleotide monophosphate, nucleotide diphosphate and nucleotide triphosphate.

25. The fluorescent compound of claim 24, wherein said protein is an antibody.

26. The fluorescent compound of claim 22, wherein said nucleic acid further comprises a probe which is a member selected from a molecular beacon, scorpion probe, sunrise probe, conformationally assisted probe and TaqMan™ probe.

27. The fluorescent compound of claim 23, wherein said enzyme is a member selected from protease, trypsin, enterokinase, HIV-1 protease, prohormone convertase, interleukin-1lb-converting enzyme, adenovirus endopeptidase, cytomegalovirus assemblin, leishmanolysin, β-secretase for amyloid precursor protein, thrombin, renin, angiotensin-converting enzyme, cathepsin-D and a kininogenase.

28. The fluorescent compound of claim 24, wherein said saccharide is dextran.

29. A method for determining whether a sample contains an enzyme, said method comprising:
   (a) contacting said sample with a peptide construct comprising
      i) a fluorescent compound of claim 1;
      ii) a quencher; and
      iii) a cleavage recognition site for said enzyme,
      wherein said peptide is in a conformation allowing donor-acceptor energy transfer between said fluorophore and said quencher when said fluorophore is excited;
   (b) exciting said fluorescent compound; and
   (c) determining a fluorescence property of said sample, wherein the presence of said enzyme in said sample results in a change in said fluorescence property.

30. A method for determining whether a compound alters an activity of an enzyme, said method comprising:
   (a) contacting a sample comprising said enzyme and said compound with a peptide construct comprising
      i) a fluorescent compound of claim 1;
      ii) a quencher; and
      iii) a cleavage recognition site for said enzyme,
      wherein said peptide is in a conformation allowing donor-acceptor energy transfer between said fluorescent compound and said quencher when said fluorescent compound is excited;
   (b) exciting said fluorescent compound; and
   (c) determining a fluorescence property of said sample, wherein said activity of said enzyme in said sample results in a change in said fluorescence property.

31. A method for detecting a nucleic acid target sequence, said method comprising:
   (a) contacting said target sequence with a detector oligonucleotide comprising a target binding sequence, said detector oligonucleotide having linked thereto,
      i) a fluorescent compound of claim 1; and
      ii) a quencher,
      wherein said detector nucleic acid is in a conformation allowing donor-acceptor energy transfer between said fluorescent compound and said quencher when said fluorescent compound is excited;
   (b) hybridizing said target binding sequence to said single-stranded target sequence, thereby altering said conformation of said detector oligonucleotide, causing a change in a fluorescence parameter; and
   (c) detecting said change in said fluorescence parameter, thereby detecting said nucleic acid target sequence.

32. The method of claim 31, wherein said complementary strand is synthesized in a target amplification reaction.

33. The method of claim 32, wherein said complementary strand is synthesized by extension of the target sequence using said detector oligonucleotide as a template.

34. The method of claim 33, wherein said fluorescence parameter is detected in-real time.

35. A method for detecting amplification of a target sequence comprising, in an amplification reaction:
   (a) hybridizing to said target sequence a detector oligonucleotide comprising a single-stranded target binding sequence and an intramolecularly associated secondary structure 5' to said target binding sequence, wherein at least a portion of said detector sequence is a single stranded tail which is available for hybridization to said target sequence, said detector oligonucleotide having linked thereto,
      i) a fluorescent compound of claim 1; and
      ii) a quencher,
      wherein said detector nucleic acid is in a conformation allowing donor-acceptor energy transfer between said fluorescent compound and said quencher when said fluorescent compound is excited;
   (b) extending said hybridized detector oligonucleotide on said target sequence with a polymerase to produce a detector oligonucleotide extension product and separating said detector oligonucleotide extension product from said target sequence;
   (c) hybridizing a primer to said detector oligonucleotide extension product and extending the primer with said polymerase, thereby linearizing said intramolecularly associated secondary structure and producing a change in a fluorescence parameter; and
   (d) detecting said change in said fluorescence parameter, thereby detecting said target sequence.

36. The method of claim 35, wherein said target sequence is amplified by a method selected from Strand Displacement Amplification, Polymerase Chain reaction, Self Sustained Sequence Replication, Transcription Mediated Amplification, and Nucleic Acid Sequence Based Amplification.

37. The method of claim 35, wherein said secondary structure further comprises a partially or entirely single-stranded restriction endonuclease site.

38. The method of claim 35, wherein a change in fluorescence intensity is detected.

39. The method of claim 38, wherein said change in fluorescence intensity is detected in real-time.

40. The method of claim 35, wherein said intramolecularly associated secondary structure comprises a portion of said target binding sequence.

* * * * *